United States Patent
Ross et al.

(10) Patent No.: US 8,185,186 B2
(45) Date of Patent: May 22, 2012

(54) SYSTEMS AND METHODS FOR TISSUE IMAGING

(75) Inventors: Brian D. Ross, Ann Arbor, MI (US); Alnawaz Rehemtulla, Plymouth, MI (US); Thomas L. Chenevert, Ann Arbor, MI (US); Charles R. Meyer, Ann Arbor, MI (US); Kuei C. Lee, San Antonio, TX (US); Kenneth Pienta, Ann Arbor, MI (US); Maha Hussein, Ann Arbor, MI (US); Anne Schott, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 795 days.

(21) Appl. No.: 12/101,753

(22) Filed: Apr. 11, 2008

(65) Prior Publication Data

US 2009/0035218 A1 Feb. 5, 2009

Related U.S. Application Data

(60) Provisional application No. 60/923,385, filed on Apr. 13, 2007.

(51) Int. Cl.
*A61B 5/055* (2006.01)
*G06K 9/00* (2006.01)
(52) U.S. Cl. ........................................ 600/410; 382/128
(58) Field of Classification Search .................. 600/410; 382/128
See application file for complete search history.

(56) References Cited

U.S. PATENT DOCUMENTS

2003/0065260 A1 * 4/2003 Cheng et al. .................. 600/427

OTHER PUBLICATIONS

Hamstra, et al. "Functional Diffusion Map as an Early Imaging Biomarker for High-Grade Glioma: Correlation with Conventional Radiologic Response and Overall Survival," American Society of Clinical Oncology, 26(20):3387-3394 (2008).
Stegman LD et al., "Diffusion MRI Detects Early Events in the Response of a Glioma Model to the Yeast Cytosine Deaminase Gene Therapy Strategy," Gene Ther. (2000) 7:1005-1010.
Taichman RS et al., "The Evolving Biology and Treatment of Prostate Cancer," (2007) J Clin Invest 117 (9) 2351-2361.
Tannock IF et al., "Docetaxel Plus Prednisone or Mitoxantrone Plus Prednisone for Advanced Prostate Cancer," (2004) N Engl J Med 351(15) 1502-1512.
Therasse P et al., "New Guidelines to Evaluate the Response to Treatment in Solid Tumors," (2000) J Natl Cancer Inst 92(3), 205-216.
Viola P et al., (1995) "Alignment by Maximization of Mutual Information," in Proceedings of 5th Int'l Conf. on Computer Vision, MIT, IEEE Press 95CH35744:16-23.

(Continued)

*Primary Examiner* — Michael Rozanski
(74) *Attorney, Agent, or Firm* — Marshall, Gerstein & Borun LLP

(57) ABSTRACT

The present invention provides systems and methods for monitoring tissue regions. In particular, the present invention provides systems and methods for detecting changes in tissue regions over a period of time. In some embodiments, the systems and methods of the present invention are used to evaluate the effectiveness of a particular treatment of a tissue region. In some embodiments, the systems and methods employ functional diffusion map algorithms for imaging changes in tissue regions over time and/or in response to therapeutic interventions.

20 Claims, 22 Drawing Sheets

OTHER PUBLICATIONS

Wilson D et al., (2004) "Radiofrequency Thermal Ablation: 3D MR Histology Correlation for Localization of Cell Death in MR Lesion Images," in Proceddings of Internat Symp Biomed Imaging, Arlington, VA: 1537-1540.

World Health Organization (1979) WHO Handbook for Reporting Results of Cancer Treatment. World Health Organization Offset Publication, Atlanta.

Zarow C et al., "A Standardized Method for Brain-Cutting Suitable for Both Stereology and MRI-Brain Co-Registration," J Neuorsci Methods 139:209-215, (2004).

Zhao M et al., "Early Detection of Treatment Response by Diffusion-Weighted H-NMR Spectroscopy in a Murine Tumour in vivo," Br J Cancer. (1996) 73:61-64.

International Search Report and Written Opinion, PCT/US2008/060092 dated Aug. 26, 2008.

Besl PJ et al., (1992), "A Method for Registration of 3-D Shapes," IEEE Trans. Pattern Analysis and Machine Intelligence 14(2):239-256.

Bookstein FL (1989), "Principal Warps: Thin-Plate Splines and the Decomposition of Deformations," IEEE Transactions on Pattern Analysis and Machine Intelligence 11(6):567-585.

Breen M et al., "Three-Dimensional Method for Comparing in Vivo Interventional MR Images of Thermally Ablated Tissue with Tissue Response," J Mag Res Imag 18:90-102, (2003).

Bubley Gj et al., (1999), "Eligibility and Response Guidelines for Phase II Clinical Trials in Androgen-Independent Prostate Cancer: Recommendations From the Prostate-Specific Antigen Working Group," J Clin Oncol 17 (11) 3461-3467.

Chenevert T.L. et al., "Diffusion Magnetic Resonance Imaging: an Early Surrogate Marker of Therapeutic Efficacy in Brain Tumors," J Natl Cancer Inst, 92:2029-2036 (2000).

Chenevert TL et al., "Diffusion MRI: A New Strategy for Assessment of Cancer Therapeutic Efficacy," Mol Imaging (2002) 1:336-343.

Chenevert TL et al., "Monitoring Early Response of Experimental Brain Tumors to Therapy Using Diffusion Magnetic Resonance Imaging," Clin Cancer Res (1997) 3:1457-1466.

Collignon, A et al., "3D Multi-Modality Medical Image Registration Using Feature Space Clustering," (1995) Lecture Notes in Computer Science 905:195-204.

Early Breast Cancer Trialists' Collaborative Group, "Polychemotherapy for Early Breast Cancer: an Overview of the Randomised Trials," 352, 930-942, The Lancet, 1998.

Evelhoch JL et al., "Applications of Magnetic Resonance in Model Systems: Cancer Therapeutics," Neoplasia. (2000) 2:152-165.

Fogelman, Ignac, et al., "Positron Emission Tomography and Bone Metastases," Seminars in Nuclear Medicine, 2005, 53 (2), 135-142.

Galons J.P. et al., "Early Increases in Breast Tumor Xenograft Water Mobility in Response to Paclitaxel Therapy Detected by Non-Invasive Diffusion Magnetic Resonance Imaging," Neoplasia 1:113-117 (1999).

Hall DE et al., "Therapeutic Efficacy of DTI-015 Using Diffusion Magnetic Resonance Imaging as an Early Surrogate Marker," Clin Cancer Res. (2004) 10:7852-7859.

Hamaoka T et al., "Bone Imaging in Metastatic Breast Cancer," (2004)J Clin Oncol 22(14) 2942-2953.

Hamstra DA et al., "Evaluation of the Functional Diffusion Map as an Early Biomarker of Time-to-Progression and Overall Survival in High-Grade Glioma," Proc Natl Acad Sci USA (2005) 102:16759-16764.

Hamstra DA et al., "The Use of 19F Spectroscopy and Diffusion-Weighted MRI to Evaluate Differences in Gene-Dependent Enzyme Prodrug Therapies," Mol. Ther. (2004) 10:916-928.

Hayward JL et al., "Assessment of Response to Therapy in Advanced Breast Cancer," (1977) Br J Cancer 35 (3) 292-298.

Hayward JL et al., "Assessment of Response to Therapy in Advanced Breast Cancer (an amendment)", (1978) Br J Cancer 38 (1) 201.

Jacobs M et al., "Registration and Warping of Magnetic Resonance Images to Histological Sections," (1999) Medical Physics 26(8):1568-1578.

Jennings D et al., "Early Response of Prostate Carcinoma Xenografts to Docetaxel Chemotherapy Monitored with Diffusion MRI," Neoplasia (2002) 4:255-262.

Jordan BF et al., "Dynamic Contrast-Enhanced and Diffusion MRI Show Rapid and Dramatic Changes in Tumor Microenvironment in Response to Inhibition of HIF-1α Using PX-478," Neoplasia (2005) 7:475-485.

Kalikin LM et al., "In Vivo Visualization of Metastatic Prostate Cancer and Quantitation of Disease Progression in Immunocompromised Mice," Cancer Biol Ther (2003) 2:656-60.

Kim B et al., "Mutual Information for Automated Unwarping of Rat Brain Autoradiographs," (1997) NeuroImage 5 (1):31-40.

Kim et al., "Correction of Local Deformations in fMRI by 3D Non-Linear Warping in Map-Slice-to-Volume Approach," Proc. Intl. Soc. Mag. Reson. Med. 8 (2000) 1765.

Latour L. et al., "Time-dependent Diffusion of Water in a Biological Model System," Proc Natl Acad Sci USA 91:1229-1233 (1994).

Lazebnik, R et al., "Volume Registration Using Needle Paths and Point Landmarks for Evaluation of Interventional MRI Treatments," IEEE Trans Med Imaging 22(5):653-660, (2003).

Lee KC et al., "Dynamic Imaging of Emerging Resistance During Cancer Therapy," Cancer Res (2006) 66:4687-92.

Lee KC et al., "Prospective Early Response Imaging Biomarker for Neoadjuvant Breast Cancer Chemotherapy," Clin Cancer Res (2007) vol. 13 No. 2 443-50.

Lyng H et al., "Measurement of Cell Density and Nectrotic Fraction in Human Melanoma Xenografts by Diffusion Weighted Magnetic Resonance Imaging," Magn Reson Med. (2000) 43:828-836.

Meyer CR (2006), "A Methodology for Registration of a Histological Slide and in Vivo MRI Volume Based on Optimizing Mutual Information," Molecular Imaging 5(1):16-23.

Meyer CR et al., "Demonstration of Accuracy and Clinical Versatility of Mutual Information for Automatic Multimodality Imaging Fusion Using Affine and Thin-Plate Spline Warped Geometric Deformations," Med Image Anal. (1997) 1:195-206.

Moffat BA et al., "Diffusion MRI Imaging in Adult Neoplasia," (2004) Cup, Cambridge: Physiological MR in Clinical Neuroscience.

Moffat BA et al., "Diffusion Imaging for Evaluation of Tumor Therapies in Preclinical Animal Models," Magma (2004) 17:249-259.

Moffat BA et al., "The Functional Diffusion Map: An Imaging Biomarker for the Early Prediction of Cancer Treatment Outcome," Neoplasia (2006) vol. 8 No. 4 pp. 259-267.

Moffat et al., "Functional Diffusion Map: A Noninvasive MRI Biomarker for Early Stratification of Clinical Brain Tumor Response," Proc Natl Acad Sci USA (2005) 102(15)5524-5529.

Park H et al., "Registration Methodology for Histological Sections and Ex Vivo Imaging of Human Prostate," Academic Radiology, vol. 15, No. 8, Aug. 2008.

Pelizzari C.A., et al., "Three Dimensional Correlation of PET, CT and MRI Images," (1987) J. Nucl. Med. 28 (4):682-683.

Petrylak DP et al., "Docetaxel and Estramustine Compared with Mitoxantrone and Prednisone for Advanced Refractory Prostate Cancer," (2004) N Engl J Med 351(15)1513-1520.

Rehemtulla A et al., "Molecular Imaging of Gene Expression and Efficacy Following Adenoviral-Mediated Brain Tumor Gene Therapy," Mol Imaging (2002) 1:43-55.

Rodrigues LM et al., "The C-neu Mammary Carcinoma in Oncomice; Characterization and Monitoring Response to Treatment with Herceptin by Magnetic Resonance Methods," Magma. (2004) 17:260-270.

Ross B.D. et al., "Assessment of the Functional Diffusion Map: An Imaging Biomarker for Early Stratification of Glioma Clinical Response," 2006 ASCO Annual Meeting Journal of Clinical Oncology (2006) vol. 24 No. 18 s 1518.

Ross BD et al., "Magnetic Resonance Imaging in Cancer Research," Eur J Cancer (2002) 38:2147-2156.

Ross BD et al., "Contributions of Cell Kill and Posttreatment Tumor Growth Rates to the Repopulation of Intracerebral 9L Tumors After Chemotherapy: An MRI Study," Proc Natl Acad Sci USA (1998) 95:7012-7017.

Ross BD et al., "Evaluation of Cancer Therapy Using Diffusion Magnetic Resonance Imaging," Mol Cancer Ther. (2003) vol. 2, pp. 581-587.

Ross BD et al., "The Role of Magnetic Resonance in the Evaluation of Cancer Therapeutics," Clin Cancer Res (1999) 5:3870s-3871s.

Roth Y et al., "High-b-Value Diffusion-weighted MR Imaging for Pretreatment Prediction and Early Monitoring of Tumor Response to Therapy in Mice," Radiology (2004) 232:685-692.

Schepkin VD et al., "Proton and Sodium MRI Assessment of Emerging Tumor Chemotherapeutic Resistance," NMR Biomed (2006) 19:1035-42.

Scher, Howard I., et al., "Prostate Cancer Clinical Trial End Points: "RECIST"ing a Step Backwards," Clin Cancer Res (2005) 11 (14), 5223-5232.

Scher, Howard I., et al., The Association Between Measures of Progression and Survival in Castrate-Metastatic Prostate Cancer, Clin Cancer Res (2007), 13 (5), 1488-1492.

* cited by examiner

Proximal    Distal

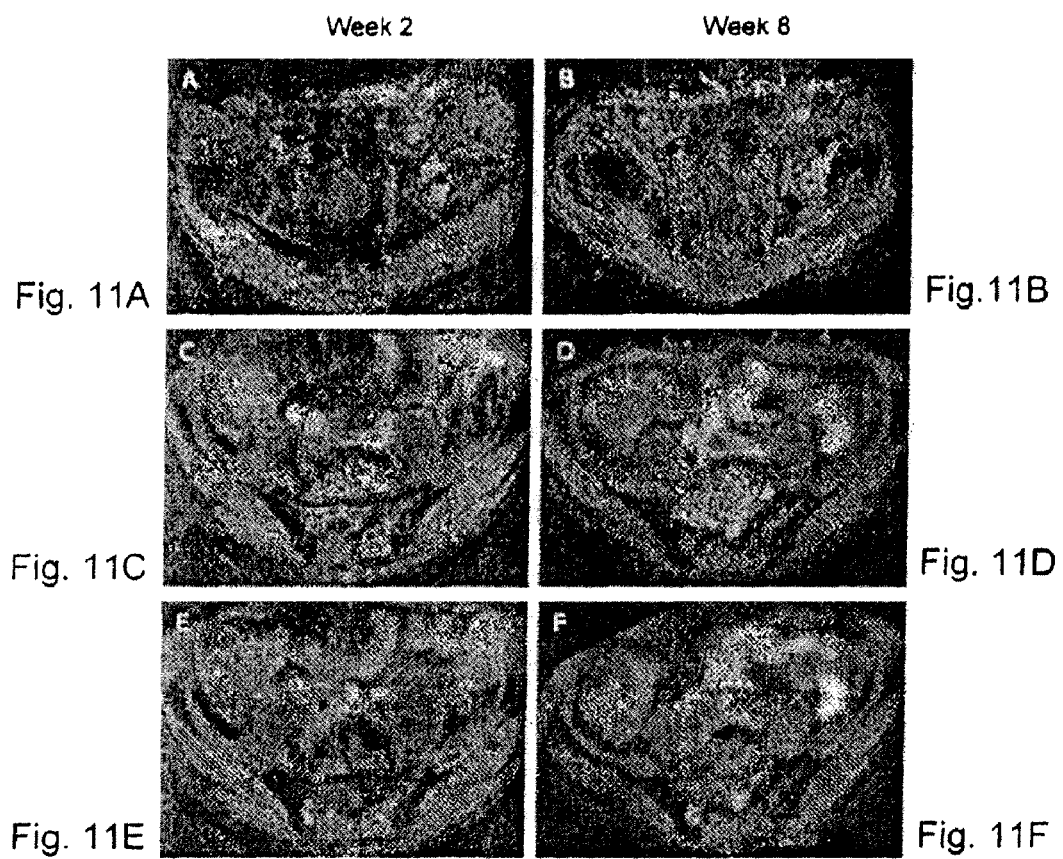

SYSTEMS AND METHODS FOR TISSUE IMAGING

This application claims priority to U.S. Provisional Patent Application No. 60/923,385, filed on Apr. 13, 2007, the contents of which are hereby incorporated by reference.

This invention was made with government support under P01CA85878, P01CA87634, P50CA93990, P50 CA69568, and R24CA83099 awarded by the National Institutes of Health. The United States government has certain rights in this invention.

FIELD OF THE INVENTION

The present invention provides systems and methods for monitoring tissue regions. In particular, the present invention provides systems and methods for detecting changes in tissue regions over a period of time. In some embodiments, the systems and methods of the present invention are used to evaluate the effectiveness of a particular treatment of a tissue region. In some embodiments, the systems and methods employ functional diffusion map algorithms for imaging changes in tissue regions over time and/or in response to therapeutic interventions.

BACKGROUND

Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer may affect people at all ages, but risk tends to increase with age. It is one of the principal causes of death in developed countries.

There are many types of cancer. Severity of symptoms depends on the site and character of the malignancy and whether there is metastasis. A definitive diagnosis usually requires the histologic examination of tissue by a pathologist. This tissue is obtained by biopsy or surgery. Most cancers can be treated and some cured, depending on the specific type, location, and stage. Once diagnosed, cancer is usually treated with a combination of surgery, chemotherapy and radiotherapy. As research develops, treatments are becoming more specific for the type of cancer pathology. Drugs that target specific cancers already exist for several types of cancer. If untreated, cancers may eventually cause illness and death, though this is not always the case.

Cancer can be treated by surgery, chemotherapy, radiation therapy, immunotherapy, monoclonal antibody therapy or other methods. The choice of therapy depends upon the location and grade of the tumor and the stage of the disease, as well as the general state of the patient (performance status). A large number of experimental cancer treatments are also under development.

Complete removal of the cancer without damage to the rest of the body is the goal of treatment. Sometimes this can be accomplished by surgery, but the propensity of cancers to invade adjacent tissue or to spread to distant sites by microscopic metastasis often limits its effectiveness. The effectiveness of chemotherapy is often limited by toxicity to other tissues in the body. Radiation can also cause damage to normal tissue.

One problem with current methods for treating the various forms of cancer is the inability to detect how well a particular type of therapy is working. For example, neoadjuvant chemotherapy in the treatment of breast cancer produces significant clinical benefit to patients (PR+CR rates>70%) (see, e.g., Early Breast Cancer Trialists' Collaborative Group Polychemotherapy for early breast cancer: An overview of the randomized trials. Lancet 352, 930-942, 1998; herein incorporated by reference in its entirety) and can be used to increase the numbers of patients eligible for a breast preservation procedure. Neoadjuvant chemotherapy has the benefit of allowing observation of chemoresponsiveness, and biological evaluation of the cancer both before and after chemotherapy administration. The ability to observe an individual's tumor response is of increasing importance in this time of rapid development of new and more targeted drugs against cancer. It is essential to determine which new drugs will benefit patients. However, clinical benefit is an endpoint that can take years to accurately determine, and therefore surrogate endpoints for clinical benefit are often used in the evaluation of new drugs. Because of its positive association with disease free survival, pathologic complete response to neoadjuvant chemotherapy has become a widely utilized surrogate endpoint for breast cancer regimens. Pathologic complete response can be evaluated approximately 3-6 months after treatment begins, but it would be useful to have a surrogate for clinical benefit that would be evaluable at an even earlier timepoint.

For example, bony metastases are a leading cause of morbidity and mortality from prostate cancer. A continuing challenge for the clinical management of this disease is the lack of imaging tools that can assess response in bone accurately (see, e.g., Scher H I, et al., (2005) Clin Cancer Res 11 (14), 5223-5232; herein incorporated by reference in its entirety). This has negatively impacted drug development in this disease (see, e.g., Scher H I, et al., (2007) Clin Cancer Res 13 (5), 1488-1492; herein incorporated by reference in its entirety). Although imaging modalities such as BS, CT, and MRI play important diagnostic and staging roles, the complex nature of osseous lesions limit the utility of these imaging technologies for accurately measuring response (see, e.g., Fogelman I, et al., (2005) Semin Nucl Med 35 (2), 135-142; herein incorporated by reference in its entirety). Part of the difficulty in using conventional anatomic imaging (CT and MRI) for assessing tumor volumetric changes as is typically accomplished in nonskeletal tumor sites for treatment response assessment is the fact that the bone undergoes constant remodeling with a strict coordination in the dynamic interaction between osteoclasts and osteoblasts to maintain proper homeostasis. Lesions residing in the bone deregulate this dynamic process and thus can present as osteolytic lesions, osteoblastic lesions, or mixed lesions when visualized by imaging, complicating interpretation and potentially confounding assessment of treatment-specific effects. As such, current recommendations on the use of these imaging techniques for monitoring treatment response widely differ depending on recommendations established from various studies, hence no consensus has been established for the validity of using BS, CT, or MRI for assessing treatment response in bone cancer patients.

As such, improved techniques for evaluating the effectiveness of a particular treatment are needed. In addition, improved techniques designed to evaluate the effectiveness of a particular treatment during the course of the treatment are needed and would provide for individualization of treatments. This would save patients from systemic toxicity from ineffective treatment and reduce costs to the health care system. Thus, further, improved techniques for evaluating candidate therapies are needed.

SUMMARY

The present invention provides systems and methods for monitoring tissue regions. In particular, the present invention provides systems and methods for detecting changes in tissue regions over a period of time. In some embodiments, the systems and methods of the present invention are used to evaluate the effectiveness of a particular treatment of a tissue region.

In some embodiments, the systems and methods employ functional diffusion map algorithms for imaging changes in tissue regions over time and/or in response to therapeutic interventions. In particular, the systems and methods of embodiments of the present invention permit the assessment of water diffusion changes within a tissue region (e.g., malignant tumor) over a period of time for purposes of evaluating the integrity of the tissue region. For example, a measured increase in water diffusion for a tissue region may indicate that the malignant tumor is undergoing cellular destruction. For example, a measured decrease in water diffusion for a tissue region, on the other hand, may indicate the cellular density of the tissue region is increasing or may indicate swollen cells within the tissue region. Variations in tissue type may cause variability in observed results. Embodiments of the present invention provide diagnostic methods that interpret changes in water diffusion properties (e.g., changes that correlate to responsiveness to a treatment or changes that correlate to the tissue over time). The present invention is not limited to a particular type or kind of mechanism underlying such alterations. The use of functional diffusion maps permits such changes to be quantified and/or visualized, thereby improving the quality of treatment provided to an individual. For example, detection of bone lesions resulting from metastatic prostate cancer is particularly difficult and detecting changes in tumors in response to interventions via imaging has been unavailable. Experiments conducted during the development of embodiments of the present invention utilizing functional diffusion mapping of bone lesions demonstrated, for example, improved imaging and enhanced ability to monitor disease progression within the bone lesions. The methods are not limited to a particular type or kind of tissue region. In some embodiments, the tissue region is a whole body of a living human. In some embodiments, the tissue region is a diseased tissue region. In some embodiments, the tissue region is an organ (e.g., heart, lung, brain, skin, bone). In some embodiments, the tissue region comprises one or more tumors (e.g., a malignant tumor, a benign tumor). In some embodiments, the tissue region comprises one or more of a breast tumor, a liver tumor, a bone lesion, and/or a head/neck tumor. In some embodiments, the tissue region is not a part of the brain.

In certain embodiments, the present invention provides methods for assessing the effectiveness of a treatment for a tissue region and/or temporal or spatial evolution of untreated tissue regions. The present invention is not limited to specific methods for assessing the effectiveness of a treatment for a tissue region. In some embodiments, the methods comprise obtaining a first set of water diffusion data for the tissue region with an MRI device configured to collect diffusion MRI data, followed by administration of a treatment to the tissue region. In some embodiments, the methods further comprise obtaining subsequent sets of water diffusion data for the tissue region with the MRI device, followed by processing the first and subsequent sets of water diffusion data and plotting/displaying the results following analysis using a functional diffusion map algorithm such that a functional diffusion map for the tissue region is generated, wherein the functional diffusion map characterizes the tissue region as having altered water diffusion properties or unaltered water diffusion properties on a regional basis at different levels of spatial scale. In some embodiments, the methods further comprise assessing the effectiveness of the administered treatment. In some embodiments, the treatment is assessed effective if the functional diffusion map characterizes the tissue region as comprising regions of increased or decreased water diffusion levels, wherein the treatment is assessed ineffective if the functional diffusion map characterizes the tissue region as comprising regions of unaltered water diffusion levels (or a failure to observe a decrease in rate of increase) and/or unchanged water diffusion levels. In some embodiments, the functional diffusion map algorithm assesses the fractional volume of tissue regions exhibiting altered diffusion properties. In some embodiments, the functional diffusion map algorithm relates to the intensity of diffusion alterations in the tissue regions. In some embodiments, the functional diffusion map algorithm reflects the region exhibiting the peak change in diffusion properties. In some embodiments, the functional diffusion map algorithm reflects the temporal rate of altered diffusion properties in the tissue. In some embodiments, the functional diffusion map algorithm reflects the spatial texture represented by altered diffusion properties in the tissue.

The fDM algorithm can be used to obtain the fractional volume of tissue and/or absolute volume of tissue that has altered diffusion properties.

A medical professional may use the observed unaltered or altered water diffusion properties along with other medical information to assess the effectiveness of a particular intervention. In some embodiments, an alteration in water diffusion properties may demonstrate a successful intervention. However, in some embodiments, the degree of alteration (e.g., increased or decreased) is used to assess the effectiveness of an intervention. For example, a detected alteration may show that a drug is killing tumor cells, but may show incomplete killing which may be an undesired outcome for the patient.

The methods are not limited to a particular type or kind of tissue region (e.g., lung, prostate, breast, colon, rectum, bladder, ovaries, skin, liver, spine, bone, pancreas, cervix, lymph, thyroid, spleen, adrenal gland, salivary gland, sebaceous gland, testis, thymus gland, penis, uterus, trachea, heart, etc.). In some embodiments, the tissue region is a whole body or large portion (e.g., a body segment such as a torso or limb; a body system such as the gastrointestinal system, endocrine system, etc.; or a whole organ comprising multiple tumors, such as whole liver) of a living human being. In some embodiments, the tissue region is a diseased tissue region. In some embodiments, the tissue region is an organ. In some embodiments, the tissue region is a tumor (e.g., a malignant tumor, a benign tumor). In some embodiments, the tissue region is a breast tumor, a liver tumor, a bone lesion, and/or a head/neck tumor. In some embodiments, the tissue region is not part of the brain.

The methods of the present invention are not limited to a particular number of or order of steps. In some embodiments, the methods further comprise the step of processing the first and subsequent sets of water diffusion data with an algorithm designed to correct non-linear 3D deformations for images obtained at different time points with diffusion MRI. The methods are not limited to a particular type or kind of algorithm designed to correct non-linear 3D deformations for images obtained at different time points with diffusion MRI. In some embodiments, the algorithm designed to correct non-linear 3D deformations for images obtained at different time points with diffusion MRI is a warping algorithm.

The methods of the present invention are not limited to a particular type or kind of treatment. In some embodiments, the treatment is a pharmaceutical treatment, a vaccine treatment, a chemotherapy based treatment, a radiation based treatment, a surgical treatment, and/or a homeopathic treatment and/or combination of treatments.

In some embodiments, additional sets of water diffusion data are collected at additional time points so as to further enhance the functional diffusion map results.

In some embodiments, the processing with the functional diffusion map algorithm occurs automatically after the obtaining of the second set of water diffusion data.

In certain embodiments, the present invention provides methods for determining the tumor burden for an individual, comprising obtaining a first set of water diffusion data for a large body region or whole body comprising multiple tumors (e.g., 2 or more, 5 or more, 10 or more, 20 or more, 50 or more, etc.) with an MRI device configured to collect diffusion MRI data; obtaining a second set of water diffusion data for the large/whole region or whole body with the MRI device; processing the first and subsequent sets of water diffusion data with a functional diffusion map algorithm such that a functional diffusion map for the large/whole body region is generated, wherein the functional diffusion map images the multiple tumors within the individual, wherein the functional diffusion map characterizes the multiple tumors as having increased water diffusion levels, decreased water diffusion levels, and/or unchanged water diffusion levels; and determining the change in tumor burden for the large/whole region. In some embodiments, the method further comprises the step of processing the first and subsequent sets of water diffusion data with an algorithm designed to correct non-linear 3D deformations for images obtained at different time points with diffusion MRI (e.g., a warping algorithm). In some embodiments, the methods further comprise obtaining additional sets of water diffusion data for the large/whole region. In some embodiments, the processing with the functional diffusion map algorithm occurs automatically after the obtaining of the second set of water diffusion data.

In certain embodiments, the present invention provides methods for treating an individual diagnosed with cancer or assessing a therapy, comprising identifying a treatment designed to target a tissue region within the individual, wherein the tissue region comprises a tumor, and wherein the tissue region is not a brain tissue region; obtaining a first set of water diffusion data for the tissue region with an MRI device configured to collect diffusion MRI data; administering the treatment to the individual; obtaining subsequent sets of water diffusion data for the tissue region with the MRI device; processing the first and subsequent sets of water diffusion data with an functional diffusion map algorithm such that a functional diffusion map for the tissue region is generated, wherein the functional diffusion map characterizes the tissue region as having unaltered water diffusion levels, altered water diffusion levels; assessing the effectiveness of the administered treatment, wherein the treatment is assessed effective if the functional diffusion map characterizes the tissue region as comprising regions of altered water diffusion levels, wherein the treatment is assessed ineffective if the functional diffusion map characterizes the tissue region as comprising regions of unaltered water diffusion level; and adapting the treatment, wherein the adapting includes discontinuing the treatment if the functional diffusion map characterizes the treatment as ineffective, wherein the adapting comprises continuing the treatment if the functional diffusion map characterizes the treatment as effective.

In some embodiments, the present invention provides a system configured to carry out any of the methods described herein. In some embodiments, the system comprises one or more of: an MRI device, a computer system comprising a processor configured to analyze data from the MRI device, and an imaging device for displaying analyzed data. As used herein the terms "processor," "digital signal processor," "DSP," "central processing unit" or "CPU" are used interchangeably and refer to a device that is able to read a program (e.g., algorithm) and perform a set of steps according to the program. In some embodiments, the processor is configured to process images obtained with diffusion MRI into a functional diffusion map. In some embodiments, the processor is configured to process diffusion MRI based images with an algorithm designed to correct non-linear 3D deformations for images obtained at different time points (e.g., a warping algorithm). In some embodiments, the system further comprises a computer memory for storing data. In some embodiments, the system comprises a processor configured to generate and control a user interface. In some embodiments, the user interface permits a user of the system to collect data, view processed data, select subsets of data, view previously collected data, and the like. In some embodiments, the system comprises a processor that controls automated data handling. For example, in some embodiments, the system the processor receives data from the MRI device (directly or indirect, including communication of data over a distance using an electronic communication network) and upon receipt or at a user command or at predetermined time frame, initiates a data analysis program that processes the data with an algorithm to generate analyzed data.

BRIEF DESCRIPTION OF THE DRAWINGS

FIG. 11 shows functional diffusion maps. Regional changes of ADC are plotted on the image to provide a visual representation of areas with increased ADC, decreased ADC, and areas where ADC did not change significantly. fDM analysis of the femoral head lesion at (A) 2 and (B) 8 weeks after treatment initiation revealed distinct regions of red voxels signifying areas with significant increases in ADC (>26_ 10_6 mm2/s). fDM analysis of the sacral lesion at (C) 2 and (D) 8 weeks after treatment revealed significant regions of increased ADC as depicted. fDM analysis of the ilium lesion at (E) 2 and (F) 8 weeks after treatment show large regions of increased ADC values.

DETAILED DESCRIPTION

Figure 1A:
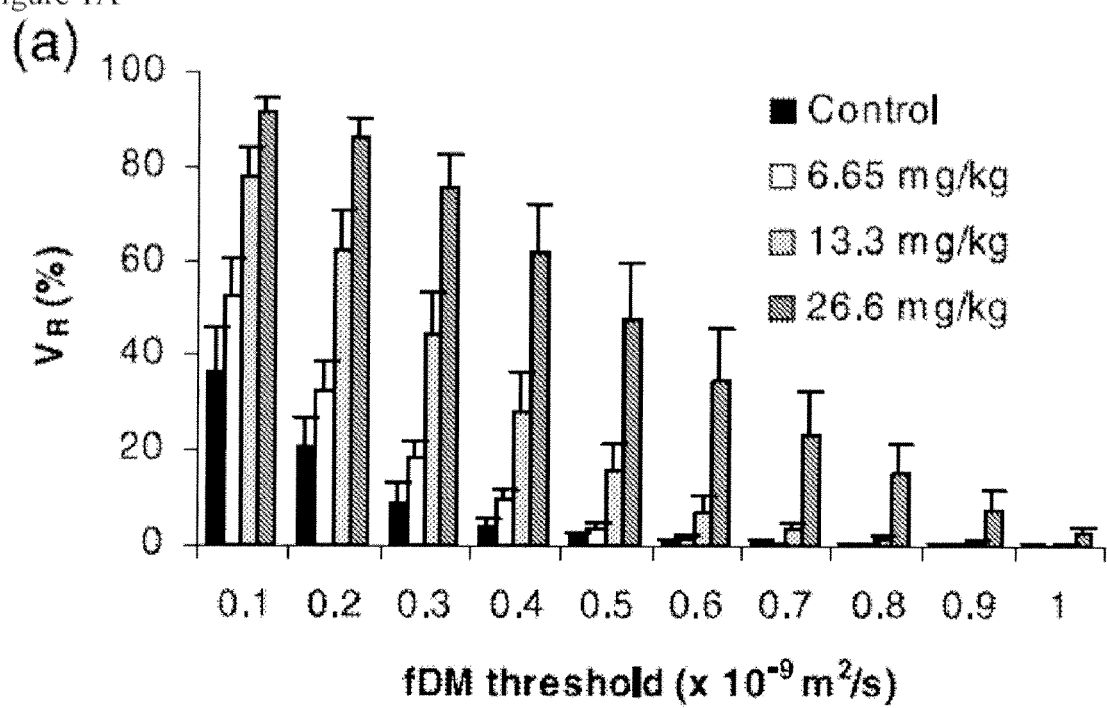
FIG. 1 shows fDM region volumes as a function of fDM threshold for the different treatment groups of rat 9L tumors. (a) The change in tumor volume of diffusion increase (i.e., $V_R$) as a function of the upper threshold of ADC change ($m^2$/sec). (b) The change in tumor volume of diffusion decrease (i.e., $V_B$) as a function of the lower threshold of ADC change ($m^2$/sec). The bars represent the mean $V_R$ and $V_B$ for each group at a given threshold, and the error bars represent the standard error of the mean.

The present invention provides systems and methods for monitoring tissue regions. In particular, the present invention provides systems and methods for detecting changes in tissue regions over a period of time. In some embodiments, the systems and methods of the present invention are used to evaluate the effectiveness of a particular treatment of a tissue region.

The present invention is not limited to the monitoring of a particular tissue region. In some embodiments, the tissue region is within a living subject (e.g., dog, cat, human, gorilla, cow, sheep, rat, mouse, etc.) (e.g., mammal, reptile). In some embodiments, the tissue region is within a living human being. In some embodiments, the tissue region is a diseased tissue region (e.g., a malignant tumor, a benign tumor, an abnormal growth, an inflamed region, a cancerous region, an infected region, an organ rejection). In some embodiments, the tissue region is a body region of the subject (e.g., lung, bone, heart, leg, foot, stomach, brain, neck, liver, breast). In some embodiments, the tissue region is the entire body of the subject.

The present invention is not limited to a particular type or manner of monitoring a tissue region (e.g., tumor region). In some embodiments, the monitoring of a particular tissue region is accomplished through obtaining data measurements for the tissue region at different time points (e.g., two time points, three time points, five time points, fifty time points, etc.) (e.g., before treatment, during treatment, after treatment) and the characterization of changes within the tissue region between data measurements. The present invention is not limited to a particular method for characterizing changes within the tissue region between data measurements. In some embodiments, the characterization involves detecting changes within the tissue region (e.g., changes in size of the tissue region, changes in density of the tissue region, changes in composition of the tissue region, changes in the diffusion directionality (anisotropy) in the region, etc.). In some embodiments, the characterization involves evaluating the effectiveness of a treatment directed toward the tissue region.

The present invention is not limited to the measurement of a particular type of data for a tissue region (e.g., malignant tumor). In some embodiments, the tissue region is imaged at different time points for purposes of characterizing the tissue region. In some embodiments, the imaging is used to determine morphological and/or anatomical changes within the tissue region. In some embodiments, the imaging is used to determine water diffusion values for the tissue region (e.g., apparent diffusion coefficient values—ADC values).

The present invention is not limited to a particular type or kind of magnetic resonance imaging. In some embodiments, the magnetic resonance imaging utilized in the present invention is diffusion magnetic resonance imaging (diffusion MRI). Diffusion MRI is a technique which measures changes in the Brownian motion of water within a tissue region (see, e.g., Latour, L., et al., Proc Natl Acad Sci USA, 91: 1229-1233, 1994; herein incorporated by reference in its entirety) (which in turn reflects underlying cellular necrosis and apoptosis) and has been utilized to predict treatment response in both pre-clinical and clinical settings where it has been demonstrated to be an early and robust biomarker for subsequent tumor response (see, e.g., Chenevert, T. L., et al., Clin Cancer Res, 3: 1457-1466, 1997; Chenevert, T. L., et al., J Natl Cancer Inst, 92: 2029-2036, 2000; Galons, J. P., et al., Neoplasia, 1: 113-117, 1999; each herein incorporated by reference in their entireties). For example, diffusion of water within a tumor is reduced in the presence of cellular membranes that act to impede the random motion of water molecules. During the course of successful treatment, loss of tumor cells and/or tumor cell membrane integrity occurs, which will then result in a reduction in the barriers that impede mobility of water molecules. Indeed, the large number of water molecules contained within a tissue region (e.g., a tumor region) provides an opportunity to quantify the respective random trajectories (e.g., diffusion or Brownian motion) of the water molecules with diffusion MRI for use as a noninvasive microscopic probe to assess changes in, for example, tumor cell membrane integrity following a treatment intervention (e.g., a pharmaceutical intervention).

Accordingly, in some embodiments, diffusion MRI is used to collect images of a tissue region (e.g., a malignant liver tumor) for purposes of characterizing changes in water diffusion values between image measurements (e.g., before and during the course of a treatment). In particular, the use of diffusion MRI permits the collection of three-dimensional tissue images (e.g., tumor images) where the MR signal is dependent on the mobility of water molecules within the tissue of interest (e.g., a breast tumor) (see, e.g., Le Bihan D, et al., Radiology. 1986; 161:401-407; herein incorporated by reference in its entirety). Water can reside within a restricted environment within a tissue which would have a lower apparent water mobility (diffusion value) than water located in a lesser restricted environment. Changes in these environments will significantly affect the overall mobility of water within that measured tissue region on the diffusion M R image. Treatment of, for example, a tumor with an effective cytotoxic agent (e.g., chemotherapy) will result in an increase in the unrestricted environment invoked by a loss of cell membrane integrity and subsequent loss in overall cellular density. Relative tissue contrast on diffusion tumor maps is directly related to diffusion values for each voxel in the image; therefore, the overall net effect of a successful treatment would be an increase in the fractional volume of the more unrestricted region, resulting in an increase in water diffusion.

In some embodiments, tissue region image measurements with diffusion MRI is used in evaluating the effectiveness of a treatment directed toward the tissue region through monitoring of the water diffusion values for the tissue region. For example, diffusion MRI can be used to assess the treatment effect through quantification of the amount of increased apparent diffusion coefficient (ADC) values in tumor regions experiencing a loss of cellular density. As such, water mobility within a tumor will increase over time following effective treatment, as represented by an increase in MRI-quantified ADC values, with the magnitude of the change related to the effectiveness of the therapy. In some embodiments, as diffusion MRI measures water diffusion within the tissue region, increased water diffusion for the tissue region indicates decreased cell membrane integrity for the tissue region. In the case of a tumor, a decrease in sufficient numbers of cells may indicate the integrity of the tumor is diminishing which indicates a successful treatment. On the other hand, a lack of change in cell membrane integrity between diffusion MRI measurements indicates the integrity of the tumor has not changed or may be increasing, thereby indicating an unsuccessful treatment. As such, utilization of diffusion MRI for monitoring tissue regions during the course of a treatment is an invaluable tool for a physician as it permits nearly immediate evaluation of the treatment earlier than tradition volumetric measures based upon anatomical images and earlier than clinical outcome measures such as time to progression or survival.

The application of diffusion MRI for the detection of early tumor treatment response was first reported using a rodent glioma model (see, e.g., Ross BD, et al., J Magn Reson Biol Med. 1994; 1:89-106; herein incorporated by reference in its entirety). Subsequent publications have verified and expanded this initial report using several different tumor models and therapeutic agents (see, e.g., Zhao M, et al., Br J. Cancer. 1996; 73:61-64; Chenevert T L, et al., Clin Cancer Res. 1997; 3:1457-1466; Ross B D, et al., Clin Cancer Res. 1999; 5:3870s-3871s; Galons J P, et al., Neoplasia. 1999; 1:113-117; Lyng H, et al., Magn Reson Med. 2000; 43:828-836; Chinnaiyan A M, et al., Proc Natl Acad Sci USA; Evelhoch J L, et al., Neoplasia. 2000; 2:152-165; Stegman L D, et al., Gene Ther. 2000; 7:1005-1010; Chenevert T L, et al., J Natl Cancer Inst. 2000; 92:2029-2036; Ross B D, et al., Eur J. Cancer. 2002; 38:2147-2156; Rehemtulla A, et al., Mol Imaging. 2002; 1:43-55; Chenevert T L, et al., Mol Imaging. 2002; 1:336-343; Jennings D, et al., Neoplasia. 2002; 4:255-262; Ross B D, et al., Mol Cancer Ther. 2003; 2:581-587; Moffat, B A., et al., Diffusion MR imaging in adult neoplasia. Gillard J, Waldman A, Barker P., editors. CUP, Cambridge: Physiological MR in Clinical Neuroscience; 2004; Hall D E, et al., Clin Cancer Res. 2004; 10:7852-7859; Hamstra DA, et al., Mol Ther. 2004; 10:916-928; Moffat BA, et al., Magma. 2004; 17:249-259; Rodrigues LM, et al., Magma. 2004; 17:260-270; Jordan BF, et al., Neoplasia. 2005; 7:475-485; Roth Y, et al., Radiology. 2004; 232:685-692; each herein incorporated by reference in their entireties). Taken together, these studies demonstrate that diffusion MRI is a sensitive biomarker that is capable of detecting early cellular changes in treated tissue regions (e.g., tumors), which precede macroscopic volumetric response.

Generally, methods for evaluating the effect of a treatment on a particular tissue region involve comparing the mean ADC value from an entire tumor mass posttherapy to the baseline (pretreatment) mean ADC value. However, such methods are limited as the response of ADC to cytotoxic therapy in the clinical setting may be more complex due to heterogeneity observed within human tumors (see, e.g., Chenevert T L, et al., J Natl Cancer Inst. 2000; 92:2029-2036; herein incorporated by reference in its entirety). For example, during the treatment of patients with, for example, malignant brain tumors, it was shown that diffusion changes could both increase due to a reduction in restricted environment and decrease due to an increase in restricted environment over time within the same tumor volume, especially for treatments with modest efficacy (see, e.g., Chenevert T L, et al., J Natl Cancer Inst. 2000; 92:2029-2036; Moffat B A, et al., Proc Natl Acad Sci USA. 2005; 102:5524-5529; each herein incorporated by reference in their entireties). This complicated response scenario rendered the use of the mean change in overall tumor ADC values less sensitive due to opposite and competing effects. Diffusion MRI has been shown to be a sensitive technique that allows for the identification of spatially distinct regional responses to therapy within, for example, tumor tissues (see, e.g., Rehemtulla A, et al., Mol Imaging. 2002; 1:43-55; Chenevert T L, et al., Mol Imaging. 2002; 1:336-343; Ross B D, et al., Mol Cancer Ther. 2003; 2:581-587; Moffat, B A., et al., Diffusion MR imaging in adult neoplasia. Gillard J, Waldman A, Barker P., editors. CUP, Cambridge: Physiological MR in Clinical Neuroscience; 2004; Hall D E, et al., Clin Cancer Res. 2004; 10:7852-7859; Moffat BA, et al., Magma. 2004; 17:249; each herein incorporated by reference in their entireties).

In some embodiments, the present invention provides systems and methods for monitoring different regions within a tissue region over a period of time (e.g., the time course of a treatment). In some embodiments, the monitoring of different regions within a tissue region over a period of time (e.g., the time course of a treatment) is accomplished through use of functional diffusion mapping (fDM) of the tissue region. Analysis of a tissue region with fDM permits, for example, a 3-dimensional voxel-by-voxel evaluation of the heterogeneity of treatment response within, for example, a tumor—a result which provides far more information than anatomical MRI scans (see, e.g., Moffat B A, et al., Proc Natl Acad Sci USA. 2005; 102:5524-5529; Hamstra D A, et al., Proc Natl Acad Sci USA. 2005; 102:16759-16764; each herein incorporated by reference in their entireties). Indeed, fDM was developed as a statistical approach for segmenting tissue regions (e.g., tumors) based on a defined threshold of ADC change following therapy (see, e.g., Moffat B A, et al., Proc Natl Acad Sci USA. 2005; 102:5524-5529; herein incorporated by reference in its entirety).

fDM has been shown to be successful in monitoring brain tumors over the course of a treatment. For example, results from patients with primary malignant brain tumors were analyzed using the fDM approach, which revealed that the volume of fDM response had a strong correlation with the overall clinical response based on the World Health Organization response criteria (see, e.g., Moffat B A, et al., Proc Natl Acad Sci USA. 2005; 102:5524-5529; Hamstra D A, et al., Proc Natl Acad Sci USA. 2005; 102:16759-16764; each herein incorporated by reference in their entireties). In addition, patients with grade III/IV gliomas analyzed using fDM revealed that fDM could be used to stratify patients as responsive or nonresponsive to a therapy in as early as 3 weeks into a 6-week to a 7-week fractionated therapy schedule (see, e.g., Hamstra D A, et al., Proc Natl Acad Sci USA. 2005; 102: 16759-16764; herein incorporated by reference in its entirety). As such, fDM has emerged as a predictive biomarker for the early stratification of rigid body tumor response before therapy completion.

Although fDM has been used to evaluate treatments directed toward brain tumors, fDM has not been utilized to evaluate treatments directed toward tumors outside of brain tumors (e.g., breast tumors, liver tumors, bone lesion tumors, neck tumors). Accordingly, the present invention provides systems and methods for monitoring tissue regions (e.g., tumors) outside of the brain through use of fDM. The present invention is not limited to a particular type or kind of tissue region outside of the brain. In some embodiments, tissue regions outside of the brain include, but are not limited to, breast tumors, liver tumors, bone lesion tumors, head and neck tumors, lung tumors, testicular tumors, organs (e.g., heart, stomach, liver, lung, skin), body regions (e.g., arms, legs, lower torso, spine, gastrointestinal region) etc.

In some embodiments, the present invention provides methods for evaluating the effectiveness of a treatment directed toward a primary bone lesion or resulting from metastasis (e.g., metastasis from prostate cancer, metastasis from breast cancer, etc.) comprising use of fDM. The mortality rate for prostate cancer is directly related to the development of metastatic disease, which is incurable, thus requiring the development of improved therapies (see, e.g., Taichman R S, et al., (2007) J Clin Invest 117 (9) 2351 2361; herein incorporated by reference in its entirety). One of the main limitations in evaluating new treatments for metastatic PCa is the inability to use available clinical imaging modalities to assess treatment response in bone, which is the predominant and often the only site of metastasis in 85% to 90% of patients (see, e.g., Petrylak D P, et al., (2004) N Engl J Med 351 (15), 1513-1520; Tannock I F, et al., (2004) N Engl J Med 351 (15), 1502-1512; each herein incorporated by reference in their entireties). Currently, assessments of tumor response in bone using criteria defined by the International Union Against Cancer (see, e.g., Hayward J L, et al., (1977) Br J Cancer 35 (3), 292-298; Hayward J L, et al., (1978) Br J Cancer 38 (1), 201; each herein incorporated by reference in their entireties), the World Health Organization (see, e.g., World Health Organization (1979). WHO Handbook for Reporting Results of Cancer Treatment. World Health Organization Offset Publication, Atlanta; herein incorporated by reference in its entirety), and the Response Evaluation Criteria in Solid Tumors (RECIST) (see, e.g., Therasse P, et al., (2000) J Natl Cancer Inst 92 (3), 205-216; herein incorporated by reference in its entirety) group do not meet the needs of oncologists in clinical practice (see, e.g., Hamaoka T, et al., (2004) J Clin Oncol 22 (14), 2942-2953; herein incorporated by reference in its entirety). In fact, the RECIST system considers bone disease to be unmeasureable. Traditional clinical assessment of bony metastases is achieved through radionuclide bone scintigraphy. Although considered to be the standard screening technique for assessing the entire skeleton for metastases, it is well recognized that this imaging technique lacks the specificity needed to accurately distinguish metastatic lesions from areas of abnormal radionuclide uptake due to inflammation, degeneration, or trauma, as well as to measure early therapeutic response. Although the use of bone scintigraphy, computed tomography (CT), and magnetic resonance imaging (MRI) plays a distinct role in identifying and characterizing the extent of disease, the use of these techniques for the assessment of treatment response is limited. To overcome these limitations, prostate-specific antigen (PSA) alterations have been explored as a screening tool for antitumor effect. A decline in PSA of at least 50% is a widely accepted measure for antitumor effect; however, the use of PSA endpoints have not been prospectively validated as fulfilling surrogacy requirements for clinical benefit in any setting (see, e.g., Bubley G J, et al., (1999) J Clin Oncol 17 (11), 3461-3467; herein incorporated by reference in its entirety). As such, development and validation of an imaging technology capable of reliably and accurately measuring antitumor effect in metastatic bone disease would provide a significant advance and aide in the timely investigation of new therapeutic agents not only for PCa but also for other malignancies common to the bone (i.e., metastatic breast cancer and primary bone cancers). Embodiments of the present invention overcome this limitation within the art. Experiments conducted during the development of embodiments for the present invention demonstrated that fDM is a sensitive and reliable method for assessing early changes in tumor response to treatment of lesions residing in the bone.

The present invention is not limited to a particular manner of implementing fDM within a tissue region. In some embodiments, the present invention provides fDM algorithms configured to correlate diffusion MRI measurements for a tissue region (see, e.g., Hamstra, D. A., et al., PNAS 2005 102(46):16759-16764; Moffat, B. A., et al., PNAS 2005 102(15) 5524-5529; each herein incorporated by reference in their entireties). In some embodiments, an fDM algorithm is provided in a system with an MRI device such that upon imaging of a particular tissue region with the MRI device an fDM image automatically generated. In some embodiments, the fDM algorithm is configured to automatically generate fDM for a particular tissue region (e.g., a tissue region that is non-responsive to certain treatments) (e.g., cell tracking). In some embodiments, an fDM for a particular tissue region distinguishes between regions within the tissue region with increased water diffusion, decreased water diffusion, and unchanged water diffusion. In some embodiments, such distinguished changes are presented within a tissue region image as color differences (e.g., red indicating increased water diffusion, blue indicating decreased water diffusion, green indicating unchanged water diffusion) (e.g., varied color or other gradient schemes distinguishing between, for example, ultra-high water diffusion alteration, moderately-high water diffusion alteration, minimally-high water diffusion alteration, and no water diffusion alteration) (see, e.g., Examples I-V). As such, fDM permits the assessment of a treatment not only for a tissue region but for specific regions of a tissue region. As such, in some embodiments, fDM is used to more aggressively target tissue regions that have been unresponsive to treatments.

In some embodiments, prior to conducting an fDM analysis for a tissue region, the images are processed with an algorithm configured to correct non-linear 3D deformations for images obtained at different time points with diffusion MRI for a tissue region. Generally, local field induced deformations are encountered in functional MRI and it is important to respond to the deformations locally rather than with time-consuming and ineffective global fits. Indeed, previous studies utilizing functional diffusion mapping involved tumors situated in rigid environments (e.g., the brain) and did not employ non-linear 3D deformation corrections. Experiment conducted during the development of some embodiments of the present invention demonstrate that non-linear 3D deformation correction find use in providing enhanced information and is important to obtain desired results. The present invention is not limited to a particular type or kind of algorithm configured to correct non-linear 3D deformations for images obtained at different time points with diffusion MRI for a tissue region. In some embodiments, non-linear 3D deformations for images obtained at different time points with diffusion MRI for a tissue region are corrected with a warping algorithm (see, e.g., Meyer C R, et al., Med Image Anal. 1997; 1:195-206; Kim, et al., Proc. Intl. Soc. Mag. Reson. Med. 8 (2000) 1765; Meyer, C R, (2006) Molecular Imaging 5(1): 16-23; Kim, B, et al., (1997) NeuroImage 5(1):31-40; Collignon, A, et al., (1995) Lecture Notes in Computer Science 905: 195-204; Viola, P, et al., (1995) Alignment by maximization of mutual information, in Proceedings of $5^{th}$ Int'l. Conf. on Computer Vision, MIT, IEEE Press 95CH35744: 16-23; Bookstein, F L (1989) IEEE Transactions on Pattern Analysis and Machine Intelligence 11(6):567-585; Jacobs, M, et al., (1999) Medical Physics 26(8):1568-1578; Pelizzari, C A, et al., (1987) J. Nucl. Med. 28(4):683; Besl, PJ, et al., (1992) IEEE Trans. Pattern Analysis and Machine Intelligence 14(2):239-256; Lazebnik, R, et al., IEEE Trans Med Imaging 22(5):653-660; Breen, M, et al., J Mag Res Imag 18:90-102; Wilson, D, et al., (2004) M Breen, R Lazebnik, S Nour, J Lewin (2004) Radiofrequency thermal ablation: 3D MR histology correlation for localization of cell death in MR lesion images, in Proceedings of Internat Symp Biomed Imaging, Arlington, Va.: 1537-1540; Zarow, C, et al., J Neurosci Methods 139:209-215; Park, H, et al., M Piert, A Kahn, R Shah, H Hussain, J Siddiqui, C Meyer (2008) Registration methodology for histological sections and ex vivo imaging of human prostate, Academic Radiology (accepted for publication); each herein incorporated by reference in their entireties). In some embodiments, the algorithm configured to correct non-linear 3D deformations (e.g., the warping algorithm) is provided as part of the system such that upon imaging of a tissue region with an MRI device the algorithm configured to correct non-linear 3D deformations automatically corrects non-linear 3D deformations prior to processing with the fDM algorithm.

In some embodiments, the present invention provides methods for measuring an individual's total body tumor burden or tumor burden in large areas of a body (e.g., lung, prostate, breast, colon, rectum, bladder, ovaries, skin, liver, spine, bone, pancreas, cervix, lymph, thyroid, spleen, adrenal gland, salivary gland, sebaceous gland, testis, thymus gland, penis, uterus, trachea, heart, etc.) through use of fDM. Generally, tumor burden refers to the number of tumors within an individual's body. In such embodiments, the individual's entire body or a large/whole area is assessed through fDM at different time points, and the total number, size, and/or other characteristics of tumors identified and analyzed. In some embodiments, the characterization of the identified tumors involves providing a status for each tumor at the different time points (e.g., increasing in size; decreasing in size) (e.g., responding to a treatment form; not responding to a treatment form). In some embodiments, the characterization involves a whole body assessment based on, for example, the averaged status of the tumors within the individual. In some embodiments, whole body fDM permits a medical professional (e.g., an oncologist) to provide a prognosis of a medical condition (e.g., a prognosis for cancer treatment based on the whole body fDM) based upon the individual's characterized tumor burden.

In some embodiments, the present invention provides methods of treating a diseased tissue region (e.g., a malignant tumor). In such embodiments, a diseased tissue region is administered a treatment directed toward the particular tissue region, and the treatment monitored over the course of the treatment with fDM. In some embodiments, a particular type of treatment is changed if the fDM indicates that the tissue region is not responding to the treatment. In some embodiments, the type of treatment is changed if the fDM indicates that the tissue region is responding to the treatment. Changes include, but are not limited to, changes in drugs or interventions, changing doses, and/or adding or subtracting drugs from a treatment cocktail.

In some embodiments, the present invention provides methods for screening the effectiveness of types of treatment of diseased tissue regions (e.g., malignant tumors, benign tumors, etc.). In such embodiments, types of treatment (e.g., pharmaceutical treatment, radiation based treatment, chemotherapeutic treatment, radiation sensitizer treatment, gene therapy based treatment, cancer vaccine based treatment) designed to treat a particular tissue region are evaluated based upon the ability to effectively treat (e.g., reduce the size of a tumor; increase water diffusion within the tissue region) the tissue region as measured with fDM at various time points. In some embodiments, treatments identified as effective in treating a tissue region (e.g., a malignant tumor) as measured with fDM may be used to treat similar types of diseased tissue regions in the same individual and/or in other individuals presenting similar diseased tissue regions.

In some embodiments, fDM is used to characterize an individual's disease (e.g., provide an overall prognosis). For example, fDM databases for similar tissue regions having similar disease patterns (e.g., liver tumors resulting from liver cancer) may be generated according to any number of variables (e.g., treatment response; water diffusion change over a certain amount of time; overall treatment outcome; etc.). The fDM database can be used to generate expected treatment plans based on expected treatment outcome for such a tissue region having such a disease. In some embodiments, a health care professional obtains an fDM for a patient's tissue region during and/or after a standard course of treatment and compare the fDM with fDMs from similar tissue regions from similar types of patients. In some embodiments, such a comparison is used to fine tune a treatment plan based on the expected treatment outcome as identified in the fDM database. Indeed, as time is of the essence in the treatment of certain diseases such a database can dramatically increase the treatment efficiency for an individual.

EXAMPLES

The invention now being generally described, will be more readily understood by reference to the following examples, which are included merely for purposes of illustration of certain aspects and embodiments of the present invention, and are not intended to limit the invention.

Example I

This example describes the materials and methods for Example II.

Intracranial Tumor Implantation. All animal works were carried out in the animal facility of the University of Michigan (Ann Arbor, Mich.) in accordance with federal, local, and institutional guidelines. Intracerebral brain tumors were implanted in male Fischer 344 rats (Charles River Breeding Laboratories, Wilmington, Mass.) weighing between 125 and 150 g. Animals were anesthesized by intraperitoneal administration of a ketamine (87 mg/kg)/xylazine (13 mg/kg) mixture. A small skin incision was made over the right hemisphere, and a 1-mm-diameter burr hole was drilled through the skull. A sterile suspension of $1 \times 10^5$ 9L cells in 5 µl of serum-free medium was introduced through a 27-gauge needle inserted to a depth of 3 mm. Rats were allowed to recover after filling the burr hole with bone wax and suturing the skin closed.

Chemotherapy. Thirty-three animals with 9L tumors were entered into the study. When in vivo tumor volumes had reached 20 to 60 µl, animals were divided into four groups. Group 1 received 0.1 ml of drug vehicle (10% ethanol) and was used as a control group (n=7). Groups 2 to 4 received 6.65 mg/kg BCNU (n=7), 13.3 mg/kg BCNU (n=11), and 26.6 mg/kg BCNU (n=8), respectively, diluted in 10% ethanol. All treatments were administered by a single intraperitoneal injection on day 0. $T_2$-weighted ($T_2$, MRI transverse relaxation time) and diffusion MRI were performed every other day posttherapy to measure volumetric and cell density changes, respectively. Animal survival data were also obtained for all groups.

Diffusion MRI. Maps of tumor ADC values were acquired every other day up to 14 days posttherapy using a previously described method (see, e.g., Chenevert T L, et al., J Natl Cancer Inst. 2000; 92:2029-2036; herein incorporated by reference in its entirety). Briefly, a trace diffusion-weighted multislice spin echo sequence (with motion compensation and navigator echo) was used to acquire 13 slices with two different diffusion weightings [$b_1$=100 sec/mm$^2$; $b_2$=1248 sec/mm$^2$; image slice thickness=1 mm; image matrix=128× 128 (0-256); field of view=30×30 mm; echo time=60 milliseconds]. During all MRI procedures, the animals were anesthesized with 1.5% isoflurane, and body temperature was maintained at 37° C. using a heated water-recirculating pad. The images acquired with b1 were essentially $T_2$-weighted images, and these were used to segment the tumor from the normal brain for volumetric analysis using an "in-house" region drawing tool developed in MATLAB (Natick, Mass.).

Image Registration and fDM. An important part of fDM analysis is the registration of parametric ADC maps acquired posttherapy to baseline ADC maps acquired before treatment. Image registration was performed using an automated linear affine coregistration algorithm (MIAMI Fuse; University of Michigan, Ann Arbor, Mich.) to maximize mutual information between the two temporally distinct three-dimensional data sets (see, e.g., Meyer C R, et al., Med Image Anal. 1997; 1:195-206; herein incorporated by reference in its entirety). Following registration and tumor segmentation of voxels within the tumor both at baseline and on day 4, fDM statistics were calculated. Firstly, ADC values of voxels posttherapy were plotted as a function of baseline ADC values. These tumor voxels were then further segmented into three regions based on an upper threshold and a lower threshold of ADC change. That is, tumor voxels that had increased ADC above the upper threshold were region 1 ($V_R$, red voxels), voxels that had decreased below the lower threshold were region 2 ($V_B$, blue voxels), and all other voxels were region 3 ($V_G$, green voxels). A comparison between treatment groups and the measurement of fDM dose dependence was accomplished to optimize the sensitivity of the thresholds used ($\pm 0.4 \times 10^{-9}$ m$^2$/sec). Normalized volumes were then calculated for each animal, and group statistics were calculated.

Histopathology. In a separate study consisting of eight animals, two animals per treatment group were imaged pretreatment and again at 6 to 7 days posttherapy. Following the second imaging session, animals were euthanized, and the brains were fixed in 10% paraformaldehyde. After 48 hours, fixed tissues were transferred to 70% ethanol and embedded in paraffin. Formalin-fixed paraffin-embedded specimens were serially sectioned and slide-mounted. Sections were stained with hematoxylin and eosin (H&E) and compared to fDMs. This was accomplished to identify underlying histologic changes associated with observed regional alterations in fDMs.

Tumor Cell Kill Calculations and Statistical Analysis. The quantification of tumor cell kill from serially volumetric imaging data for each animal was accomplished as previously described (see, e.g., Ross B D, et al., Proc Natl Acad Sci USA. 1998; 95:7012-7017; herein incorporated by reference in its entirety). In brief, log(cell kill)=$\log_{10}[V_{pre}/V_{post}]$, where V represents the tumor volume from MRI. Linear least squares analysis was used to measure the statistical significance of trends in the BCNU dose dependence of fDM volume, animal survival, and log cell kill, and in the correlation of fDM response with survival and cell kill. When two groups were compared, a one-tailed Student's t test was used. Both linear least squares and Student's t test were performed using Microsoft Excel (Microsoft, Redmond, Wash.). To compare the median survival of all four animal groups, a log rank test was performed using Prism (GraphPad Software, Inc., San Diego, Calif.).

Example II

Figure 1B:
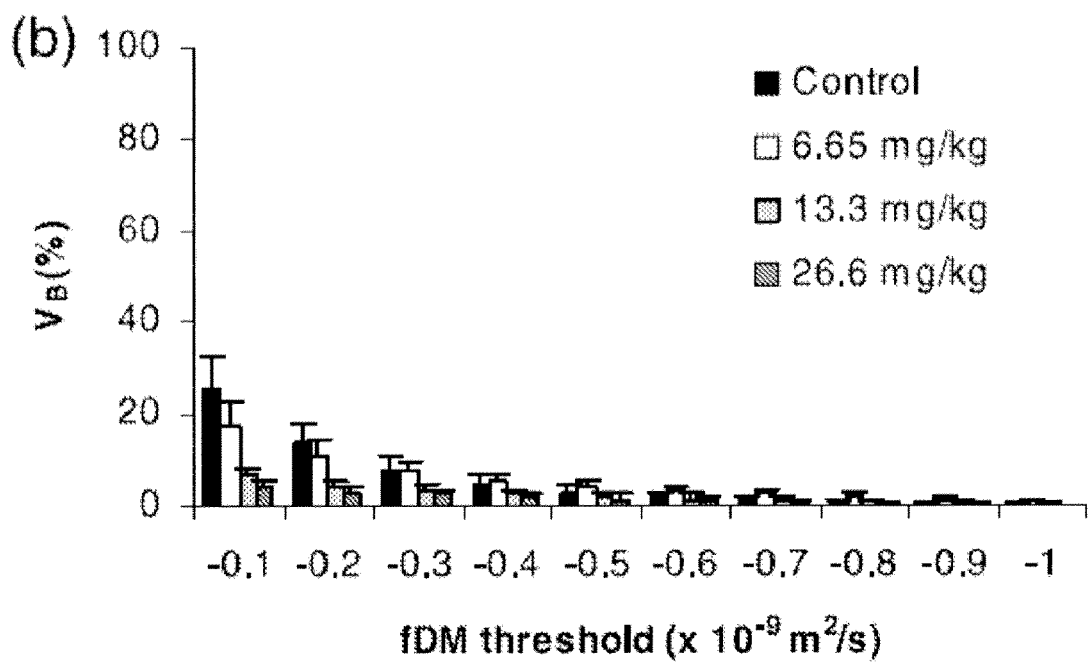

This example demonstrates the use of fDM in assessing treatment of brain tumors. Objective assignment of threshold-defining fDM regions is required to provide optimal sensitivity for the detection of therapy-induced changes. As shown in FIG. 1A, the normalized tumor volume of region 1 ($V_R$) was plotted as a function of decreasing upper threshold for the four groups of animals investigated. Analysis of these data revealed that upper thresholds of $0.2 \times 10^{-9}$, $0.3 \times 10^{-9}$, and $0.4 \times 10^{-9}$ m$^2$/sec were all able to statistically differentiate between the three treatment groups, and between the treatment groups and the control group. At these thresholds, based on a one-tailed t test, $V_R$ was statistically different (P<0.05) for all groups, with $V_R$ being greater for the 26.6-mg/kg, 13.3-mg/kg, 6.65-mg/kg, and control groups. In contrast, as shown in FIG. 1B, the same plot for the lower threshold revealed that there was no statistical difference (P>0.05) between the normalized volume of region 2 ($V_B$) for the control and the 6.65-mg/kg groups, the 6.65- and the 13.3-mg/kg groups, or the 13.3- and the 26.6-mg/kg groups. However, the higher $V_B$ values of control animals were found to be statistically significant (P<0.05) compared to the 13.3- and 26.6-mg/kg animals for thresholds of $-0.1 \times 10^{-9}$ and $-0.2 \times 10^{-9}$ m$^2$/sec. To minimize the $V_R$ and $V_B$ volumes of the control group while maintaining sensitivity to treatment-induced changes, a threshold of $\pm 0.4 \times 10^{-9}$ m$^2$/sec was used to identify/segment the three fDM regions for all fDM images, scatter plots, and subsequent statistical comparisons with outcome efficacy measures.

Functional diffusion mapping is a spatial mapping technique that segments diffusion MRI voxels within a tumor into three distinct regions of diffusion change. Region 1 consisted of voxels wherein the change in ADC values from baseline to posttherapy was greater than an upper threshold. These regions were shown as red pixels on fDM images and as red data points on fDM scatter plots. Region 2 represented voxels in which the ADC change was less than a lower threshold and was shown as blue pixels on fDM images and as blue data points on scatter plots. Region 3 comprised voxels for which ADC change was within the two thresholds and was shown as green pixels and data points. Such examples of fDM images and scatter plots were taken from a representative animal from each of the groups on day 4 posttreatment. The control tumor example demonstrated how these tumors contained mostly region 3 voxels over this time frame, with the detected changes of $V_R$ and $V_B$ representing only 2.9% and 5.7% of the total tumor volume, respectively. However, the 6.65-mg/kg tumor contained responding voxels of $V_R$=7.7% and $V_B$=2.6%, respectively. The mean $V_R$ (10.6±2.8%) and the mean ADC change (10.7±2.2) for this group were statistically significantly higher (P<0.05) than those for the control animals ($V_R$=3.9±1.7; ΔADC=−0.8±2.7%). For animals treated with 13.3 mg/kg BCNU the responding region $V_R$ (30%) was greater than for both the control and the 6.65-mg/kg-treated animals. The mean $V_R$ (28.7±8.0) and ΔADC (22.9±5.3%) were both statistically greater (P<0.05) than the values for the 6.65-mg/kg treated group. In the case of the 26.6-mg/kg BCNU-treated most of the voxels contained within the tumor mass had increased diffusion values above the threshold ($V_R$=90.6%), with only 0.3% $V_B$ voxels. The group mean $V_R$ (62.0±9.0%) and the mean ADC change (49.0±9.7%) were both statistically greater (P<0.05) than those for the 13.3-mg/kg-treated group.

Figure 2A:
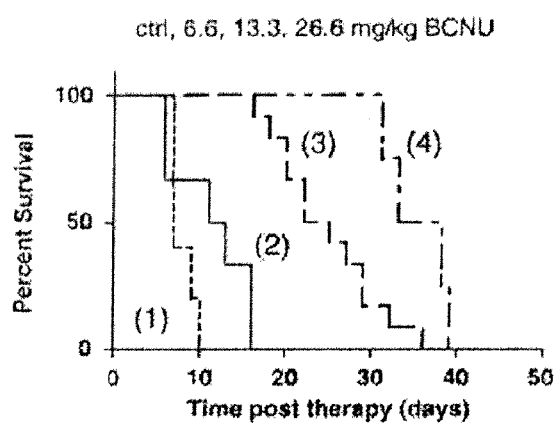
FIG. 2 shows dose dependence of traditional therapeutic efficacy measures. (a) Kaplan-Meier animal survival plots of animals treated with: (1) 0 mg/kg, (2) 6.65 mg/kg, (3) 13.3 mg/kg, and (4) 26.6 mg/kg BCNU. The median survival for these groups was 7, 13, 23.5, and 35.5 days posttherapy, respectively. All groups were significantly different, as determined by log rank test (P<0.05). (b) Normalized tumor volume at the time fDM analysis was performed (4 days) post-treatment with BCNU as a function of dose. The gradient of the least squares fit was $-4.0\pm1.3$ (P=0.004), and the intercept was $290\pm20$ (P=$1.4\times10^{-14}$). (c) Log cell kill of the 9L tumor cells as a function of BCNU dose. The gradient of the least squares fit was $0.013\pm0.02$ (P=$3.7\times10^{-9}$), and the intercept was $-0.53\pm0.21$ (P=0.02). The error bars represent the standard error of the mean for each group.
Figure 2B:
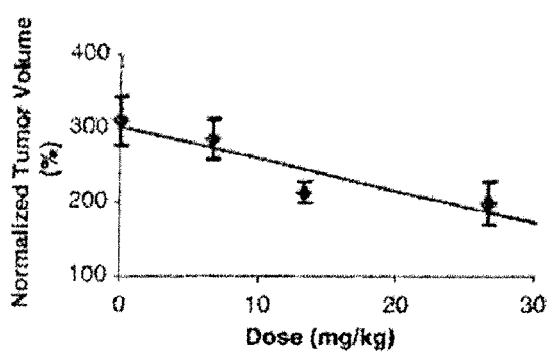
Figure 2C:
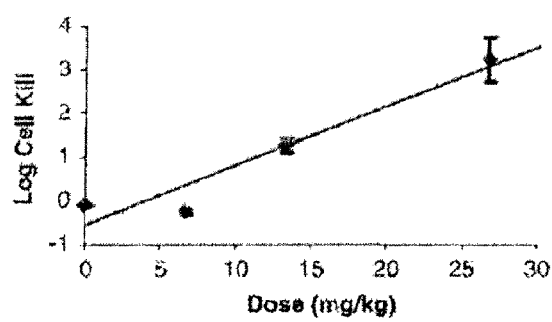

Traditional measures of brain tumor treatment efficacy were also evaluated in this study. FIG. 2A shows a survival plot for all groups of animals, revealing that there was a dose-dependent increase in animal survival relative to the control group. Using a log rank test, all groups had a statistically significant difference in median survival posttherapy (P<0.05). In addition, as shown in FIG. 2B, normalized tumor volume at 4 days posttreatment displayed a decreasing trend with increasing dose of BCNU. Although the groups were not all statistically different, the results of a linear least squares fit showed that the slope was statistically significant (P<0.05). Lastly, as shown in FIG. 2C, log cell kill showed an increasing statistical trend (P<0.05) with dose, although the 6.65-mg/kg group (−0.25±0.08) was not statistically greater (P>0.05) than the control group (−0.09±0.04). The log cell kill values of the 13.3-mg/kg (1.28±0.18) and the 26.6-mg/kg (3.22±0.51) groups were both statistically different (P<0.001) from each other and from the control group.

Figure 3A:
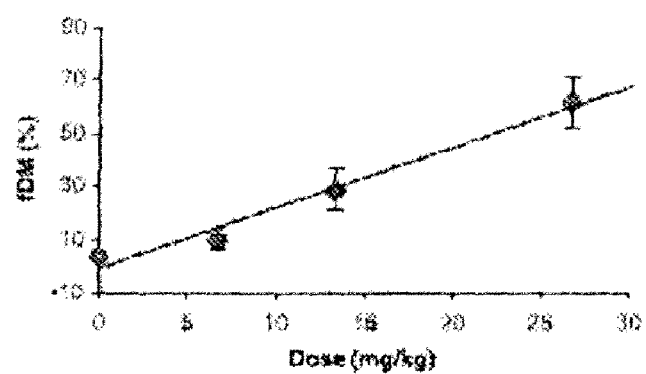
FIG. 3 shows dose dependence of traditional therapeutic efficacy measures. (a) Kaplan-Meier animal survival plots of animals treated with: (1) 0 mg/kg, (2) 6.65 mg/kg, (3) 13.3 mg/kg, and (4) 26.6 mg/kg BCNU. The median survival for these groups was 7, 13, 23.5, and 35.5 days posttherapy, respectively. All groups were significantly different, as determined by log rank test (P<0.05). (b) Normalized tumor volume at the time fDM analysis was performed (4 days) post-treatment with BCNU as a function of dose. The gradient of the least squares fit was $-4.0\pm1.3$ (P=0.004), and the intercept was $290\pm20$ (P=$1.4\times10^{-14}$). Log cell kill of the 9L tumor cells as a function of BCNU dose. The gradient of the least squares fit was $0.013\pm0.02$ (P=$3.7\times10^{-9}$), and the intercept was −0.53±0.21 (P=0.02). The error bars represent the standard error of the mean for each group.
Figure 3B:
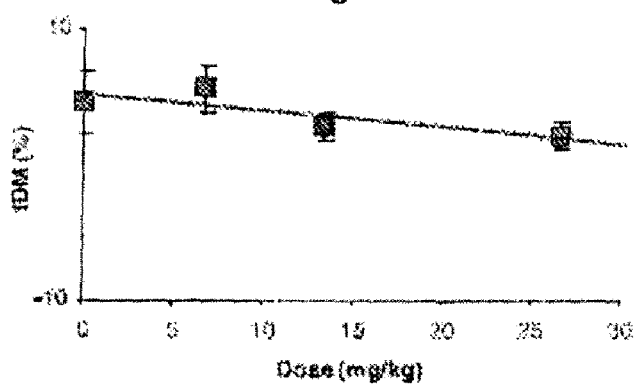

The dose dependence of fDM based on the group means (±SEM) for $V_R$ and $V_B$ values was also calculated. FIGS. 3A and 3B are plots of $V_R$ and $V_B$ as a function of drug dose (mg/kg). The resulting "best-fit" gradient (2.30±0.40 kg/mg) revealed that $V_R$ was linearly correlated extremely well (P=5.8×10$^{-6}$) with BCNU dose. In contrast, $V_B$ revealed very little correlation (P=0.87) with drug dose. Based on these results, it was apparent that, for treatment of the 9L tumor with BCNU, the fDM parameter that was most sensitive to drug-induced cellular changes was $V_R$. This parameter was then used for the statistical evaluation of fDM with additional outcome measures.

Figure 4A:
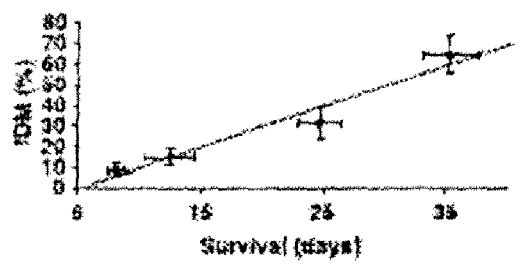
FIG. 4 shows a correlation plot of fDM $V_R$ changes with animal survival and cell kill. (a) $V_R$ volumes calculated 4 days post-BCNU therapy are plotted as a function of the median survival for each of the treatment groups. The error bars represent the standard error of the mean for each group. The gradient of the least squares fit was 1.55±0.44 (P=0.002), and the intercept was −6.2±9.8 (P=0.53). (b) Change in percent fDM versus log cell kill measured using MRI tumor volume measurements over time.
Figure 4B:
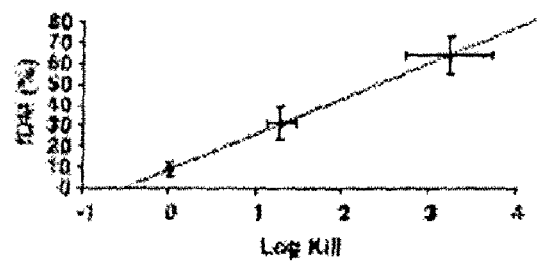

The ability of fDM to predict subsequent therapeutic outcome, as quantified by overall animal survival, was evaluated. FIGS. 4A and 4B display plots of percent fDM change (using the parameter $V_R$) versus mean animal survival (days post-treatment). The resulting gradient (1.55±0.44, P=0.002) showed that $V_R$ correlated very well with overall animal survival. This finding strongly supports the use of fDM as a biomarker that is capable of predicting early the overall outcome (survival) following treatment administration.

The fDM approach provides interesting spatial information not provided for in the mean change in ADC approach. The underlying histologic basis for the observed changes in the detected $V_R$ and $V_B$ fDM regions was investigated following treatment with 6.67 mg/kg BCNU. Histologic evaluation of the tumor section prepared from this image region was undertaken. A magnified view of the histologic section of the low-diffusion ($V_B$) region (high restriction of water mobility) was found to have very high cellular density. In fact, this region contained 153 active mitoses as counted from 10 high-power fields (original magnification, ×40 objective lens). This is reflective of, for example, a region with a very high rate of cellular proliferation. In distinct contrast, the region identified by fDM as having very low restricted water diffusion ($V_R$) was identified by histology to have moderate cellular density. This region was found to have a lower level of cellular proliferation (96 mitoses in 10 high-power fields) than the $V_B$ region.

Example III

This example describes the materials and methods for Example IV.

Cell Lines. PC3 cells were transfected with a luciferase-encoding pLazarus retroviral construct using Fugene 6 (Roche Applied Science, Indianapolis, Ind.) as per manufacturer's instructions. Wildtype PC3 cells were cultured in RPMI-1640 supplemented with 10% FBS whereas transfected cells (PC3$^{Luc}$) were maintained in selection media supplemented with 200 µg/ml G418 (Invitrogen; Carlsbad, Calif.).

Mice. Male SCID mice (Charles River Laboratories, Wilmington, Mass.) were housed in specific pathogen free rooms at The University of Michigan AAALAC, International accredited facilities. For implantation of PC3$^{Luc}$ cells, mice were anesthetized with 1.75% isofluorane/air anesthesia and 2×10$^5$ cells in 100 µl of sterile Dulbecco's PBS lacking Ca$^{+2}$ and Mg$^{+2}$ (DPBS) were administered into the left ventricle of the heart.

Bioluminescence Detection. Approximately 4 to 5 weeks after PC3$^{Luc}$ implantation, animals were screened using bioluminescence to select subjects exhibiting metastatic disease. Subsequently, animals were divided into untreated control (n=11) and docetaxel treated (n=9; 40 mg/kg/wk×3) groups. Bioluminescence studies were initiated prior to treatment for baseline values and performed throughout the experiment. For these studies, mice were anesthetized with a 2% isofluorane/air mixture and given a single i.p. dose of 150 mg/kg D-luciferin (Promega; Madison, Wis.) in normal saline. Animals were then re-anesthetized using 2% isofluorane/air mixture approximately 8 mins post administration of D-luciferin and images were acquired approximately 10 to 12 mins post D-luciferin administration. For image acquisition, a CCD camera system (Xenogen; Alameda, Calif.) with a nose-cone isofluorane delivery system and heated stage for maintaining body temperature was used. Results were analyzed using Living Image® software provided with the Xenogen imaging system. Signal intensity was quantified as the sum of all detected photon counts within a uniform region-of-interest (ROI) manually placed during data post processing.

Magnetic Resonance Imaging. A subset of control (n=5) and docetaxel treated (n=7) animals from the bioluminescence screening study, which had evidence of focal metastases within the leg, were entered into the MR studies. For MRI examination, mice were anesthetized with a 2% isofluorane/air mixture and maintained at 37 C, using a heated water bed, inside a 9.4-T Varian MR scanner (120-mm clear horizontal bore, Varian, Palo Alto, Calif.) and a double-tuned volume radiofrequency coil. A trace diffusion-weighted multi-slice spin echo sequence was used to acquire 15 slices with two different diffusion weightings ($b_1$=184 s/mm$^2$, $b_2$=1106 s/mm$^2$, slice thickness=0.5 mm, image matrix=64×128, field of view=15×15 mm; TE=40 ms, TR=3.5 s). The z-gradient first moment was zeroed to reduce the dominant source of motion artifact as well as a 32-point navigator echo was prepended to each phase-encode echo. The phase deviation of each navigator echo relative to their mean was subtracted from the respective image echoes prior to the phase-encode Fourier transform. Images were acquired prior to treatment and subsequently 2 times per week. The low b-factor images were essentially T2-weighted to allow tumor volume measurements. The tumor boundary was manually defined on each slice and then integrated across slices to provide a volume estimate.

Image Registration and fDM. An important part of fDM analysis is the registration of post-treatment ADC maps to baseline pretreatment ADC maps. Image registration was performed using an automated linear affine coregistration algorithm to maximize mutual information between the two temporally distinct three-dimensional data sets (see, e.g., Meyer C R, et al., Med Image Anal 1997; 1: 195-206; herein incorporated by reference in its entirety). Following registration and segmentation of voxels within the tumor both at baseline and on day 4, fDM statistics were calculated (I-Response™, Cedara Software, Mississauga, Ontario). Firstly, ADC values of voxels post therapy were plotted as a function of baseline ADC values. These voxels were then further segmented into three regions based on an upper and lower threshold of ADC change. Tumor voxels with an ADC increase above the upper threshold were depicted as red, whereas voxels that had decreased below the lower threshold were depicted as blue. All other voxels that did not change significantly were depicted as green.

Histopathology. Approximately 2 weeks post-treatment initiation, selected animals from the control (n=2) and docetaxel treated (n=2) groups were sacrificed immediately after acquisition of MR data and tumor bearing legs were harvested for staining. Tissue sections (5 µm thickness) were stained with hematoxylin and eosin using routine protocols. The histopathology results were then compared to fDM using distinguishable landmarks as well as dimensional analysis.

Example IV

Figure 5A:
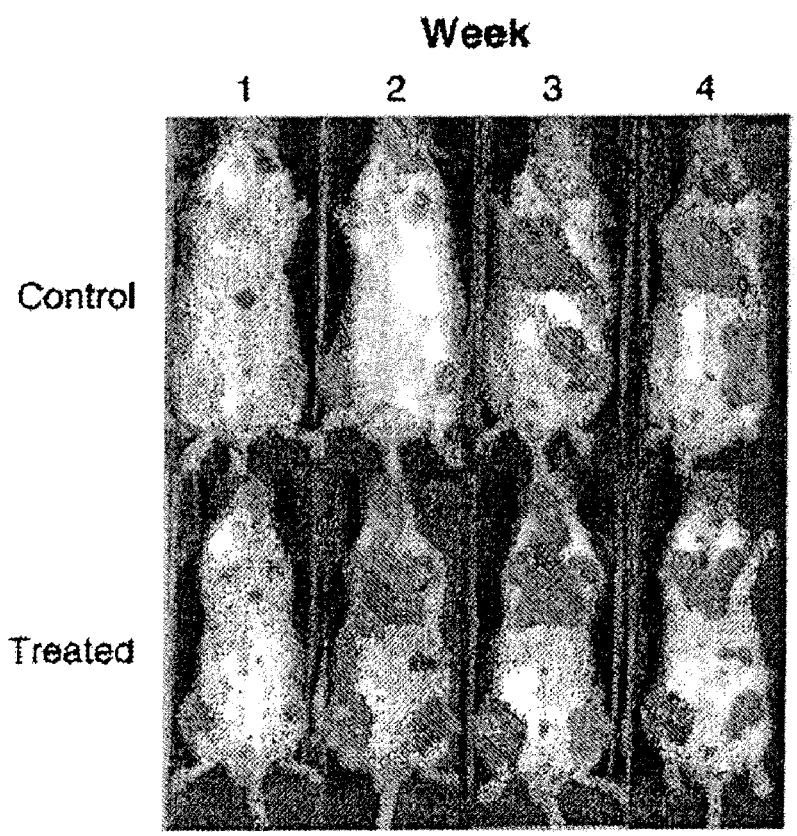
FIG. 5 shows bioluminescence imaging of control and treated animals. A) Representative images from control (top panels) and treated (bottom panels) animals from week 1, 2, 3, and 4. B) The mean of normalized photons from control (n=11) and treated (n=9) groups on day 0, 7, 14, and 21 post-treatment initiation were calculated and plotted. Error bars represent the standard error of the mean.
Figure 5B:
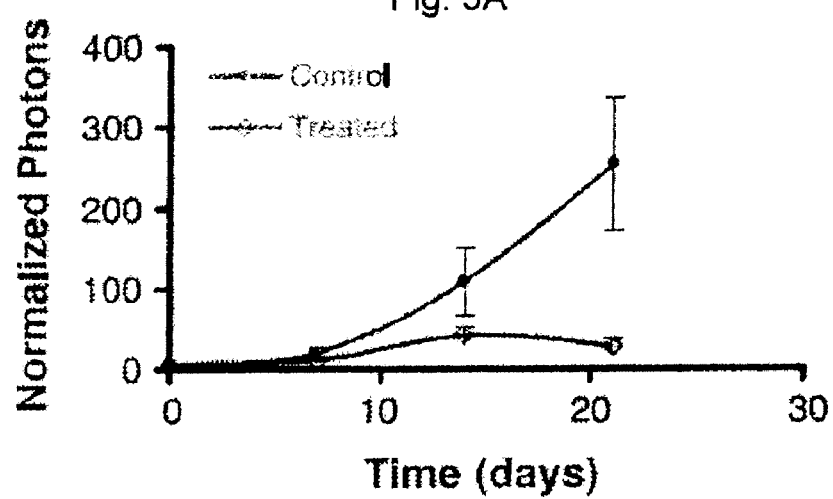

This example demonstrates the use of fDM in assessing treatment of bone lesions resulting from metastatic prostate cancer. For these experiments, a previously reported model of metastatic prostate cancer with a high incidence of bone involvement was employed (see, e.g., Kalikin L M, et al., Cancer Biol Ther 2003; 2:656-60; herein incorporated by reference in its entirety). As previously mentioned, this disease model was generated through intracardiac injection of human PC3$^{Luc}$ tumor cells stably expressing firefly luciferase into SCID mice. Approximately 4 weeks post injection of PC3$^{Luc}$ cells, bioluminescence detection was employed to monitor differences in luciferase activity between control and treated groups. Serial images from representative control and treated animals are provided in FIG. 5A. For the control animal, luciferase activity continued to markedly rise from week 1 to 4. However, in the representative treated animal, despite an initial increase, luciferase activity remained relatively unchanged especially when comparing week 4 to 1. The mean photon counts from control (n=11) and treated (n=9) groups were calculated and plotted in FIG. 5B demonstrating a continuous signal increase in control animals, whereas docetaxel treated animals remained stable throughout the experiment. These results indicated that docetaxel therapy had an effect in stunting disease progression as compared to controls.

Figure 6A:
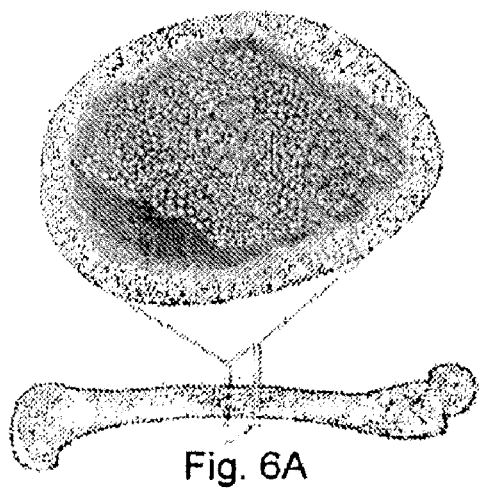
FIG. 6 shows fDM analysis of metastatic bone lesions in the tibia of SCID mice. A) Schematic of a tumor residing in the bone with a pseudo-fDM overlay generated from co-registration of diffusion MRI data pre- and post-treatment. After treatment, regional changes of ADC are plotted on the image to provide a visual representation of tumor response. The green voxels represent areas of the lesion that did not respond to therapy such that a significant change in ADC was not detected. In the event of a positive therapeutic response, loss of cellularity within responsive regions results in a significant increase in ADC ($>0.4\times10^{-9}$ m$^2$/s), which is depicted as red voxels. B) fDM analysis from a representative control animal at day 7 and 11 post initiation of PBS treatment. fDMs (top panels) from a representative control animal are provided for qualitative assessment of overall changes in tumor ADC. Scatter plots (bottom panels) were also generated and the percentage of increased ADC was determined to be 1.2% and 2.5% on day 7 and 11, respectively. C) fDM analysis from a representative treated animal at day 7, 11, 14, and 18 post initiation of docetaxel therapy. fDMs (top panels) for the representative treated animal are provided. Scatter plots (bottom panel) were also generated and the percentage of increased ADC was determined to be 4.0% (day 7), 13.1% (day 11), 30.0% (day 14), and 53.7% (day 18). D) The mean percentage of increased ADC from the control (n=5) and treated (n=7) group were calculated and plotted as a function of time post initiation of therapy. Error bars represent the standard error of the mean. E) The mean normalized volumes from control (n=5) and treated (n=7) groups were calculated and plotted as a function of time. Error bars represent the standard error of the mean.
Figure 6B:
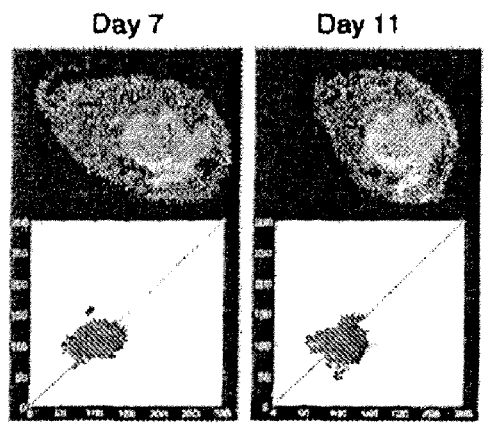
Figure 6C:
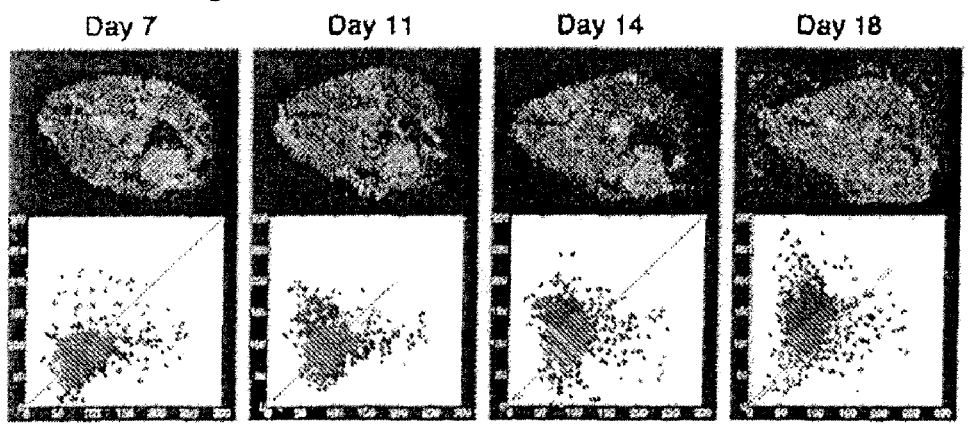
Figure 6D:
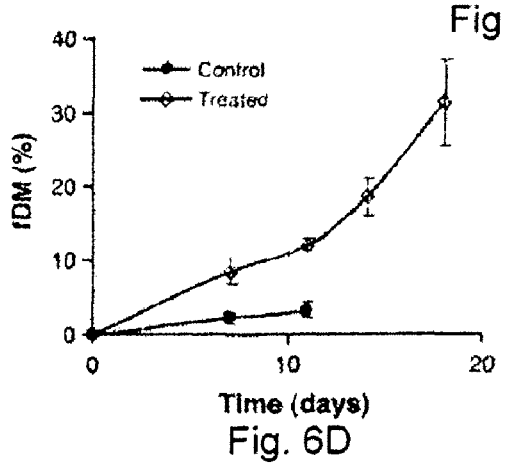
Figure 6E:
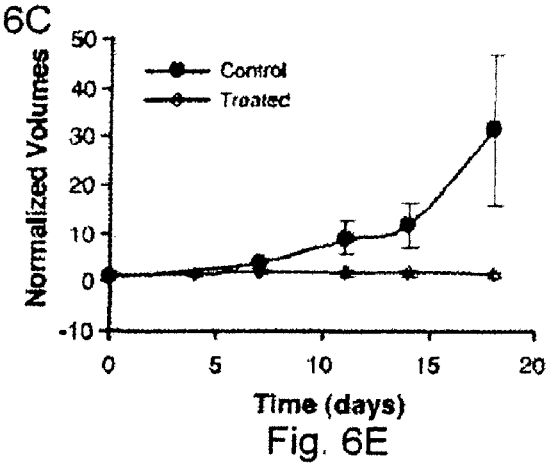

Animals that presented metastatic lesions in the leg region, based upon bioluminescence detection, were entered into the MR studies. To better illustrate the fDM approach, a representation of a bone lesion undergoing therapy is provided in FIG. 6A. During successful therapy, the loss of tumor cell viability (density) occurring regionally within the tumor mass can be spatially resolved using the fDM approach. These areas can be detected as an increased region of water mobility and fDM displays these regions of cell loss as red while regions not significantly impacted by the treatment are displayed as green (FIG. 6A). In the current study, MRI examinations were accomplished twice per week to quantify tumor volume and generate fDM data. In FIG. 6B (top panels), an fDM from a representative control animal was provided for qualitative assessment of overall changes in tumor ADC. Corresponding scatter plots (FIG. 6B, bottom panels) were also generated and the percentage of increased ADC was determined to be 1.2% and 2.5% on day 7 and 11, respectively. fDM analysis from a representative treated animal at day 7, 11, 14, and 18 post initiation of docetaxel therapy was also performed as shown in FIG. 6C. fDMs (FIG. 6C, top panels) for the representative treated animal revealed an increase in regions of red voxels over time, and corresponding scatter plots (FIG. 2C, bottom panel) determined the regions of increased ADC to be 4.0% (day 7), 13.1% (day 11), 30.0% (day 14), and 53.7% (day 18). Mean changes in tumor diffusion, as determined by fDM, from control (n=5) and treated (n=7) groups were plotted in FIG. 6D. Control animals revealed insignificant change in diffusion values whereas treated animals revealed progressively increasing fDM diffusion changes (red regions) over the three week treatment period. A statistically significant difference in fDM values between control and treated animals was achieved as early as 7 days post-treatment (p<0.05; FIG. 6D). MRI determination of tumor volumes revealed continued growth of control tumors throughout the experiment while treated tumors did not (FIG. 6E), which correlates with the fDM findings and indicates that docetaxel therapy was efficacious. Moreover, differences in tumor volumes between the two groups reached significance at day 11 post-treatment initiation (p<0.05), much later than was observed by fDM suggesting that fDM could serve as an early biomarker for treatment response.

Figure 7A:
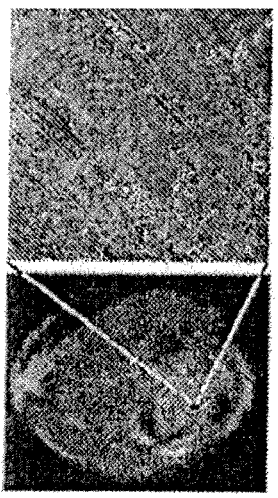
FIG. 7 shows the standard measures of treatment response. A) A representative bone lesion 14 days post injection of PBS was immediately extracted after diffusion MRI acquisition for histological analysis using H&E staining (top panel). Comparative analysis of fDM (bottom panel) and histology revealed that the green region corresponded to an area of high cellularity and density. C) H&E staining of the femur section taken 14 days post-treatment initiation revealed a bone lesion heterogeneous in density with the proximal region appearing less dense as compared to the distal region. B) The fDM image (bottom left panel) from the proximal region of the tumor suggests that a region of the lesion responded to therapy, which correlated with the corresponding H&E stained region (top left panel) revealing low cellular density. fDM analysis of the distal tumor region (bottom right panel) suggests a lack of treatment response as little change in ADC was detected. Comparative analysis of the fDM image and corresponding H&E stained section (top right panel) reveals a relatively dense cellular morphology.
Figure 7B:
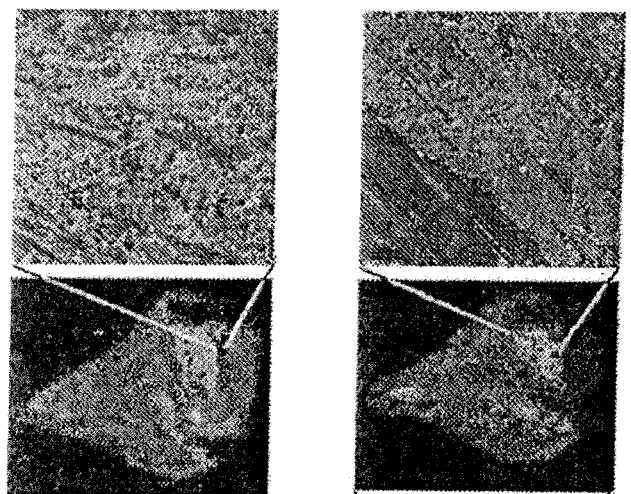
Figure 7C:
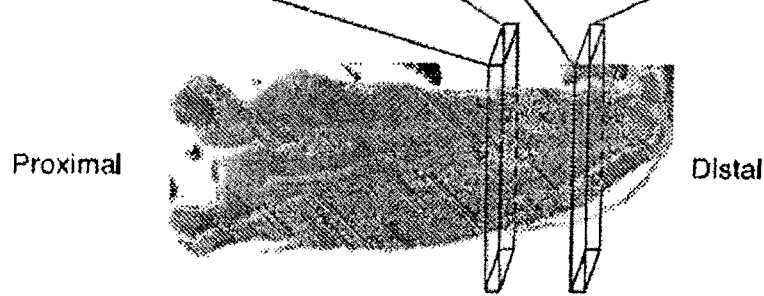

Validation of the fDM findings was accomplished through spatially correlating fDM with H&E stained histological sections from control (FIG. 7A) and treated (FIG. 7C) tumors excised 14 days following treatment initiation (see, e.g., Moffat B A, et al., Neoplasia 2006; 8:259-67; herein incorporated by reference in its entirety). For the control tumor, fDM data revealed minimal changes in tumor diffusion values, which corresponded to histological observations of a highly dense and cellular morphology (FIG. 7A). A macroscopic cross-sectional view of the leg from a treated animal (FIG. 7C) demonstrated a much more heterogeneous morphology in which regions of high and low cellularity were apparent throughout the tumor mass. The fDM image corresponding to the proximal region of the lesion with reduced cellularity demonstrated (FIG. 7B, bottom left panel) that a significant portion of the tumor mass, as depicted by the red voxels, responded to therapy. In contrast, the fDM image corresponding to the distal (FIG. 7B, bottom right panel) region demonstrated a lack of significant treatment response consistent with histological findings. Microscopic images (FIG. 7B, top left panel) from a region corresponding to an area of red voxels revealed a high degree of cellular disintegration. For comparison, a microscopic image from a region of green voxels in the distal fDM image (FIG. 7B, top right panel) revealed a relatively dense and highly cellular tumor region. Due to the lack of a non-responsive tumor to serve as a negative control, the possibility exists that the observed fDM changes could be due to secondary effects of docetaxel therapy rather than a distinct anti-tumor effect. However, previous results have clearly and reliably demonstrated that a drastic increase in tumor water diffusion values is directly correlated with an underlying decrease in cellular density resulting from a positive therapeutic response (see, e.g., Moffat B A, et al., Neoplasia 2006; 8:259-67; Lee K C, et al., Clin Cancer Res 2007; 13:443-50; each herein incorporated by reference in their entireties). Moreover, previous studies have also demonstrated that diffusion MRI was able to ascertain the loss of anti-tumor effect and emergence of drug resistance when resistant tumors exhibited decreased diffusion change upon further treatment with an initially effective therapy (see, e.g., Lee K C, et al., Cancer Res 2006; 66:4687-92; Schepkin V D, et la., NMR Biomed 2006; 19:1035-42; each herein incorporated by reference in their entireties). As such, the observed fDM changes in this prostate cancer model appear consistent with the anticipated anti-tumor effects of docetaxel therapy, which correlated both temporally and spatially with the histopathogical findings. These histological and diffusion findings taken together demonstrate that the fDM imaging biomarker is capable of detecting spatially distinct changes in tumor cellularity in response to therapeutic intervention.

Example V

This example demonstrates the use of fDM in assessing treatment head and neck cancer. Patients presenting with head and neck tumor were tested. Data were collected before and after treatment and were processed using a warping algorithm. Following treatment, patients were categorized as responsive (CR; complete response) to therapy or non-responsive (no response or PR; partial response). The fDM data correlated to patient outcomes. In particular, $V_B$ and $V_T$ (where $V_T=V_R+V_B$) values were substantially higher in non-responders than responders, providing a marker for assessing therapy effectiveness and for monitoring patient status. Additionally, it was observed that non-responders had a higher pretreatment mean apparent diffusion coefficient (ADC), showing that pretreatment data may be used as a predictive measure of patient outcome.

Example VI

This example describes the materials and methods for Examples VII-X.

Patient Information A hormone-naïve 68-year-old male with newly diagnosed metastatic PCa was consented and was enrolled into the study. He was initiated on combined androgen blockade with bicalutamide and goserelin acetate. Magnetic resonance imaging scans were acquired at weeks 0 (baseline), 2, and 8 following treatment initiation which were used to generate the Functional Diffusion Maps at the 2 and 8 week time intervals. Due to pain and pathologic fracture, the patient was also treated with palliative radiation therapy encompassing the sacrum and ilium at 2 weeks post initiation of androgen deprivation therapy.

Clinical Correlates Serum samples were obtained at weeks 0 (baseline), 2, and 8 following treatment initiation. Prostate-specific antigen levels were quantified and expressed in grams per milliliter (g/ml) of plasma.

Bone Scintigraphy A whole-body bone scan (BS) was performed by administering 25.8 mCi of Tc-99m methylene diphosphonate (MDP) and gamma camera images of the entire skeleton obtained 4 hours later (Siemens Medical Solutions, Malvern, Pa.). Nuclear imaging was performed 2 weeks before and 2 months after initiation of androgen deprivation therapy.

Computed Tomography Computed tomography (CT) of the pelvis was performed without IV contrast on a 16-slice helical scanner (General Electric Medical Systems, Milwaukee, Wis.). Two hundred two axial sections of 2.5 mm thickness were acquired using 140 kVp, 590 mA, 0.8 sec/revolution, and a 512 matrix over a 36-cm field of view.

Magnetic Resonance Imaging Magnetic resonance imaging (MRI) examinations including diffusion-weighted and standard anatomic sequences were performed before and 2 weeks after initiation of therapy. MR imaging was performed on a 3-T scanner (Achieva model; Philips Medical Systems, Bothell, Wash.) using a quadrature body coil for transmission and a six-channel cardiac coil for reception. Standard sequences for depiction of anatomy and tumor extent included axial proton density (repetition time [TR]/echo time [TE]=2700/30 msec, two averages) turbo spin-echo and axial T2-weighted turbo spin-echo (TR/TE=7800/60 msec, two averages) with fat suppression through a short inversion time (TI=200 msec). Geometry for these sequences was as follows: field of view, 281 mm right/left by 200 mm anterior/posterior; thirty-eight 4-mm sections with a 1-mm gap; 256__232 acquisition matrix for proton density; and 248__165 for T2-weighted scans. Diffusion-weighted scans were acquired using fat-suppressed, single-shot, spinecho, echo-planar imaging to reduce motion artifact and parallel imaging (SENSE factor=2) to reduce spatial distortion. Geometry of the diffusion-weighted scans was as follows: 350 mm right/left by 302 mm anterior/posterior; thirty 5-mm sections with a 1-mm gap; 200__172 acquisition matrix; TR/TE=2000/58 msec; and 8 averages for low (b=0 sec/mm2) and 16 averages for high (b=800 sec/mm2) diffusion-sensitivity scans. Apparent diffusion coefficient (ADC) maps were calculated in the routine manner given by the logarithm of the ratio of low-b and high-b images, then scaled by the inverse of b-value difference.

Diffusion Analysis Lesions in MR images acquired at weeks 2 and 8 were coregistered to their corresponding pretreatment MR images using an automatic algorithm based on maximizing mutual information. Registration was accomplished for each individual tumor located in the sacrum, ilium, and femoral head regions after the images were cropped to localize the registration to a limited region-of-interest (ROI) containing a single lesion. Lesions were manually contoured by a radiologist who defined the ROI by inspection of all available image data. Diffusion-average data were generated for weeks 0, 2 and 8 using the ROI contours of each of the three lesions and the mean change in diffusion values were calculated. Computation of fDMs for each lesion at weeks 2 and 8 was accomplished by comparison of voxels within the tumor at weeks 2 and 8 with the pretreatment values (week 0) as previously described (see, e.g., Moffat B A, et al., (2005) Proc Natl Acad Sci USA 102 (15), 5524-5529; Hamstra DA, et al., (2005) Proc Natl Acad Sci USA 102 (46), 16759-16764; each herein incorporated by reference in their entireties) using MIAMI Fuse (University of Michigan, Ann Arbor, Mich.) (see, e.g., Meyer C R, et al., (1997) Med Image Anal 1 (3), 195-206; herein incorporated by reference in its entirety). The tumor was segmented into three different categories wherein the red voxels represent regions within the tumor where ADC values increased (>26__10__5 mm2/sec), the blue voxels represent a decreased ADC (<26__10__5 mm2/sec), and the green regions represent tumor diffusion values that were within these thresholds (e.g., unchanged). These thresholds were determined to be the 95% confidence intervals that were calculated using the variation in the adjacent muscle tissue as a test region, which should have unaltered diffusion values following registration at weeks 2 and 8 posttreatment. The percentage of tumor within each of the three categories was then calculated as VI (% red voxels), V0 (% green voxels), and VD (% blue voxels). All fDM values reported represent the values computed using VI.

Statistical Analysis Statistical analysis was accomplished using Microsoft Excel using Student's t test to compare changes in diffusion at different time points and between fDM and average ADC measurements.

Example VII

Figure 8:
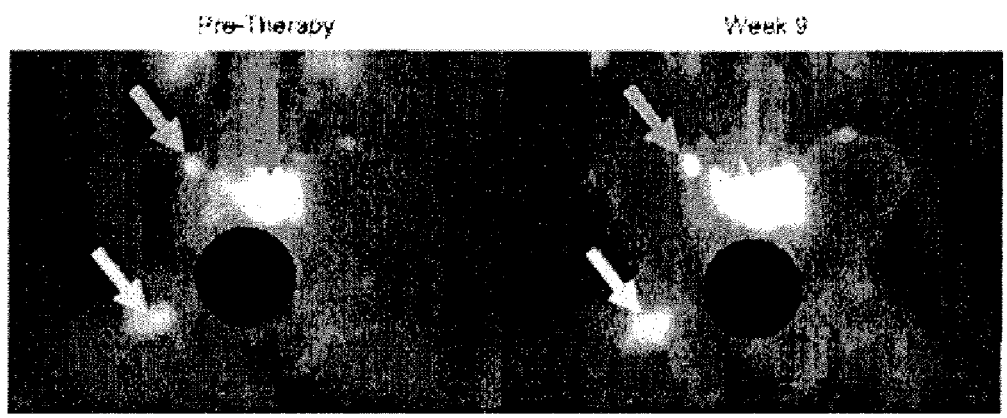
FIG. 8 shows bone scintigraphy. Posterior bone scintigraphic image of the pelvis shows increased uptake of the sacrum and left femoral head lesions, with two additional foci of uptake in each ilium. Follow-up bone scintigraphy 9 weeks after therapy shows increased intensity of the uptake.
Figures 9A, 9B, 9C, 9D:
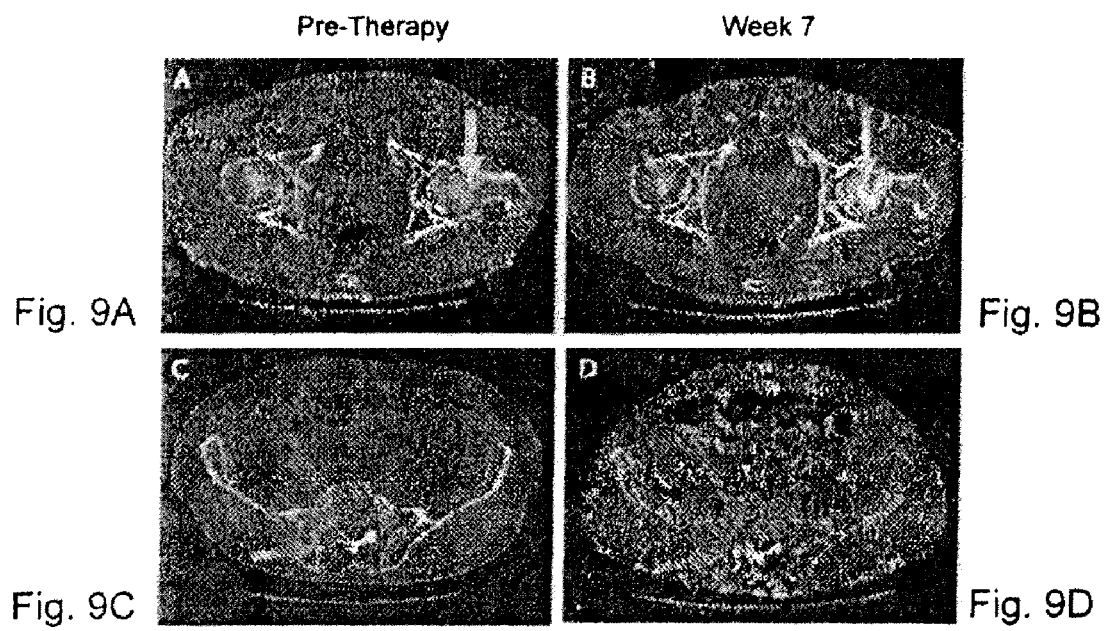
FIG. 9 shows computed tomography. Axial CT images (A) before and (B) 7 weeks after treatment show a mixed lucent and sclerotic metastasis (highest arrows) of the left femoral head. Axial CT images reveal the sacral lesion (middle arrows) and ilium lesion (lowest arrows) (C) before and (D) 7 weeks after treatment.
Figures 10A, 10B, 10C, 10D:
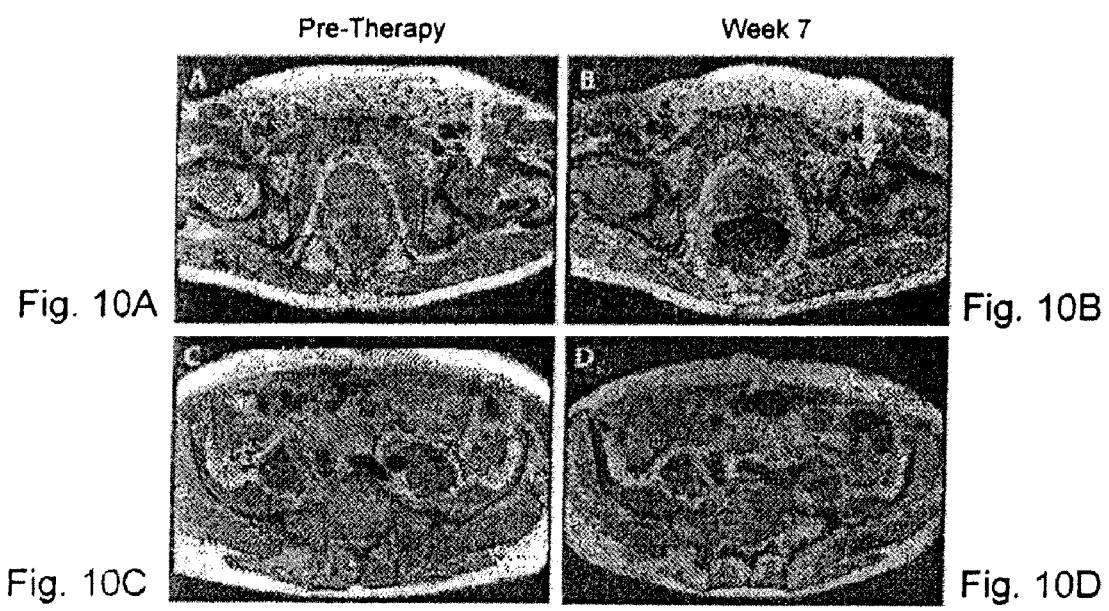
FIG. 10 shows T1-weighted MRI. Axial T1-weighted MR images of the femoral head (A) before and (B) 7 weeks after treatment show heterogeneous marrow replacement (arrow). Axial T1-weighted MR images of the sacrum (highest arrows) and ilium (lowest arrows) (C) before and (D) 7 weeks after treatment.

This example demonstrates the identification of metastatic disease and characterization of osseous lesions. At the time of initial diagnosis, the patient underwent Tc-99m MDP BS to ascertain the extent of skeletal involvement. As shown in FIG. 8, posterior BS revealed two large areas of increased uptake in the sacrum (middle arrow) and left femoral head (lowest arrow), with two additional smaller foci of uptake in each ilium (highest arrow denoting lesion analyzed by fDM). Nine weeks after initiation of androgen deprivation therapy, a follow-up BS was obtained (FIG. 8) revealing the continuing presence of previous identified lesions; however, the uptake in these regions appeared more intense with greater uptake of the radionuclide. Visualization by CT revealed mixed lucency and sclerosis within the left femoral head lesion (FIG. 9A, arrow). After receiving androgen deprivation therapy for 7 weeks, increased sclerosis was observed by CT (FIG. 9B, arrow). Computed tomographic images of the sacral lesion before treatment (FIG. 9C, highest arrow) revealed a predominantly lytic morphology within the sacrum; however, interval-increased sclerosis was observed after therapy (FIG. 9D, highest arrow). Computed tomographic images of the right ilium lesion (FIG. 9C, lowest arrow) before treatment revealed similar morphology to the lesion in the sacrum with increased sclerosis observed following treatment (FIG. 9D, lowest arrow). Further characterization of the lesions was achieved by MRI. Proton density-weighted images of the femoral head lesion revealed the presence of heterogeneous marrow replacement (FIG. 10A, arrow), with an apparent increase of low signal after 7 weeks of treatment (FIG. 10B, arrow). Similarly, the sacral and ilium lesions from proton density-weighted MR images exhibited heterogeneous marrow replacement (FIG. 10C, highest and lowest arrows, respectively), with increased low signal after treatment (FIG. 10D). Tumor volumes were quantified using ROI analysis of each of the three tumors evaluated using T2-weighted MR images at weeks 0, 2, and 8 post-treatment initiation. As shown in Table 1, tumor volumes were similar at the pretreatment time point (week 0) and at weeks 2 and 8 posttreatment. Overall, tumor volume measurements were unable to detect significant perturbations in tumor size in the 8-week timeframe following treatment initiation.

TABLE 1

Tumor Volume Measurements over Time.

| Tumor Site | Pretreatment ($cm^3$) | Week 2 ($cm^3$) | Week 3 ($cm^3$) |
|---|---|---|---|
| Femoral Head | 52.97 | 51.52 | 51.35 |
| Sacrum | 68.29 | 69.46 | 72.21 |
| Ilium | 2.34 | 2.76 | 2.56 |

Example VIII

This example demonstrates fDM analysis of osseous lesions revealing changes in tumor diffusion subsequent to therapy. Using the fDM approach, diffusion MRI data from the femoral head, sacral, and ilium lesions were analyzed to detect spatial changes in tumor diffusion. As shown in FIG. 11A, fDM analysis of tumor diffusion after 2 weeks of therapy revealed regions within the femoral head lesion that had significant increases in diffusion. Analysis revealed that 21.1% of the total analyzed volume had significant increase in ADC at week 2 posttreatment. A small region of tumor was not analyzed in this lesion due to overlap with abdominal fat signal due to inadequate fat suppression that occurred on that time interval. The sacral and ilium lesions also exhibited distinct areas of increased ADC (FIGS. 11C and 11E, respectively), which were found to be 26.4% and 24.5% of the tumor volume at 2 weeks posttreatment. After 8 weeks of therapy, fDM analysis of the femoral head, sacral, and ilium lesions again identified regions of increased diffusion values (encoded as red voxels on fDM), signifying areas of increased diffusion within these three lesions (FIGS. 11B, 11D, and 11F, respectively). Quantification of fDM scatter plots revealed regions of increased ADC to be 36.4% (femoral head lesion), 29.0% (sacral lesion), and 47.1% (ilium lesion) of the tumor volume at 8 weeks posttreatment.

Example IX

Figure 12:
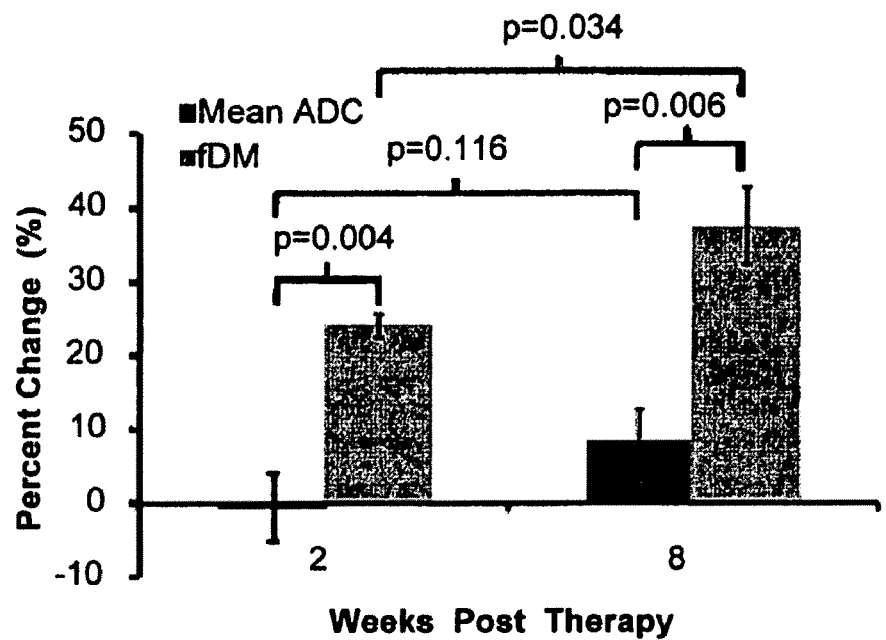
FIG. 12 shows comparison of mean ADC versus fDM with respect to pre-therapy baseline. At 2 weeks post-therapy, a decrease of 0.7±4.8% was observed by comparing mean ADC whereas fDM demonstrated a 24±1.6% increase in ADC. At 8 weeks, mean ADC increased by 8.3±4.3% whereas fDM demonstrated a 38±5.2% increase in ADC.

This example demonstrates analysis of tumor-average diffusion MRI data. Lesion-mean ADC values were generated by the average of ADC values within a volume of interest defined on each lesion. Lesion volumes of interest were defined for the femoral head, sacral, and ilium lesions. Before treatment initiation, baseline mean ADC values of the femoral head, sacral, and ilium lesions were determined to be $74.5 \times 10^{-6}$, $110.8 \times 10^{-6}$, and $78.0 \times 10^{-6}$ $mm^2$/sec, respectively. As the patient underwent treatment, the femoral head lesion exhibited little change in tumor mean diffusion where mean ADC values were determined to be $77.8 \times 10^{-6}$ $mm^2$/sec at 2 weeks and $76.8 \times 10^{-6}$ $mm^2$/sec at 8 weeks posttreatment. The sacral lesion revealed an approximate 10% decrease in mean ADC values to $99.8 \times 10^{-6}$ $mm^2$/sec at 2 weeks post-treatment initiation, which later increased by nearly 5% above baseline at 8 weeks ($116.2 \times 10^{-6}$ $mm^2$/sec). The ilium lesion revealed very little change in mean ADC at week 2 ($80.7 \times 10^{-6}$ $mm^2$/sec) and a 16.7% increase in mean ADC to $91.1 \times 10^{-6}$ $mm^2$/sec at 8 weeks post-treatment initiation. Comparison of the fDM and mean ADC analysis approaches was accomplished and the results are displayed in FIG. 12. For each tumor, the percentage change of mean ADC values from baseline was calculated at 2 and 8 weeks post-treatment initiation. The average fDM percent increase in diffusion fDM values, which represents the percent of tumor volume with increased diffusion values, was 24±1.6% and 38±5.2% at weeks 2 and 8, respectively. However, the mean percentage change from baseline for the three lesions obtained from the mean ADC analysis was −0.7±4.7% and 8.3±4.3% at 2 and 8 weeks, respectively.

Example X

This example describes clinical response assessment. PSA levels were monitored over the course of treatment. At week 0, PSA levels were 10.7 ng/ml and were significantly reduced at weeks 2 and 8 posttreatment to 1.3 ng/ml and 0.3 ng/ml, respectively. The PSA levels indicated that the patient was responding to androgen deprivation, which is also reflected in the fDM but not in the mean-derived ADC values.

Example XI

Figure 13:
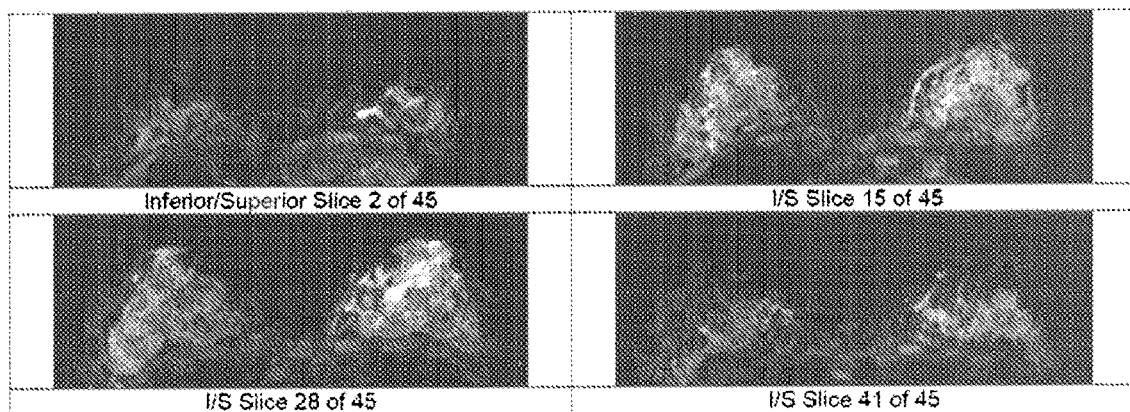
FIG. 13 shows four of 45 slices of registered breast using the b0 data from a diffusion acquisition on the 3T magnet.

This example describes warping registration of images. FIG. 13 shows the results of the interval registration of a normal breast using exams separated by 2 days. The registration is shown using a checker-board technique where alternating squares come from the reference and resulting registration of the second interval examination. For this demonstration a diffusion acquisition with the 7-channel breast coil from Philips 3.0T, i.e. the b0 acquisition, was used where the diffusion gradients are turned off; SENSE=2 was chosen to reduce artifacts. Voxel size was $0.85 \times 0.85 \times 2$ $mm^3$ and the information content of the scan was high.

Figure 14:
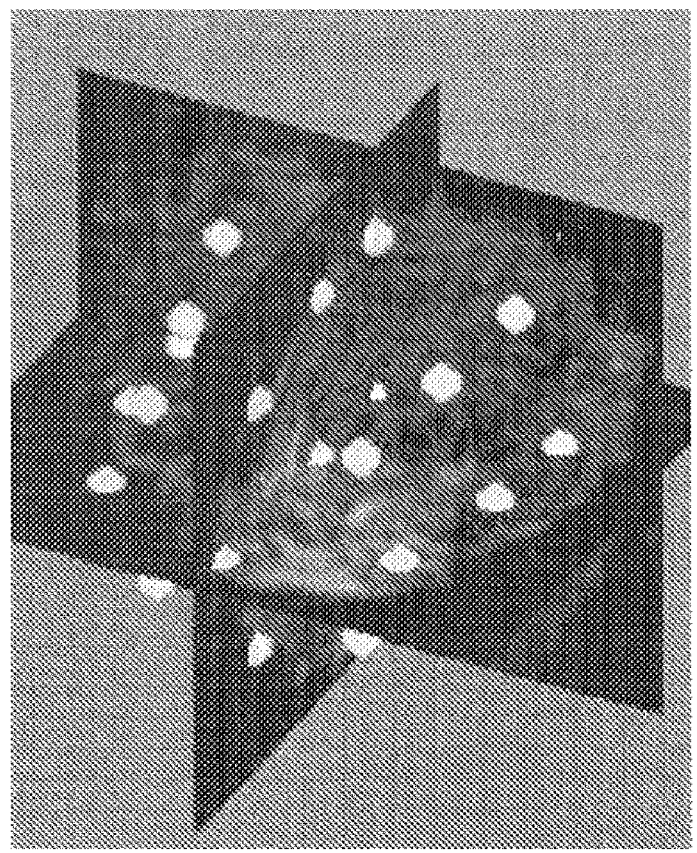
FIG. 14 shows regular 3×3×3 breast shaped array of control points placed in reference exam. Two orthogonal image planes are shown in the data set.

Warping registration was achieved by providing an automatically produced matrix of 3×3×3 control point "handles" in the reference data set based on volume bounds as seen in FIG. 14 obtained by user cropping of typically one breast in both interval exams. If both breasts were involved, each pair is registered as separate pairs after the associated cropping. The algorithm was started by automatically providing 5 approximate Inferior/Superior Slice 2 of 45 I/S Slice 15 of 45 I/S Slice 28 of 45 I/S Slice 41 of 45 homologous control points in the second (e.g., "floating"), interval exam that corresponded to the position of the first 5 control points in the reference set of 27, again based on the resultant cropping of the technician. While the reference set of points remained fixed, an optimizer moved the ones in the second set to warp the second interval exam so that it matched the reference. A crude warp was optimized using these 5 points and decimation of the data set, and then used to instantiate the first 10 points from the reference to repeat the process. After repeating the process for 15, 20, and finally all 27 points, the final solution was computed. Since each point represented 3 degrees of freedom (DOF), the final solution represented the use of 81 DOF in the warping. The choice of decimation and DOF used at each stage was controlled by a schedule that was selected/edited by a user [12]. Thin plate splines (TPS) were used to interpolate warping deformations between control point locations [28].

A simulation experiment was performed to quantify the expected capture range for interval breast MR registration. A breast MR (e.g., the b0 DWI cropped left breast volume shown in FIG. 13) was deformed in a known way, used as the second interval scan, and then registered to the deformed MR with original MR to recover the deformation. The left breast data was deformed using a perturbed uniform grid of 3×3×2=18 control points using TPS as the geometric interpolant. Zero mean Gaussian noise of varying standard deviation was added to the location of control points to realize a known, random deformation. A total of 65 known deformations were generated using standard deviation values between 3 and 15 with resulting mean deformations between 2 and 24 mm.

Figure 15:
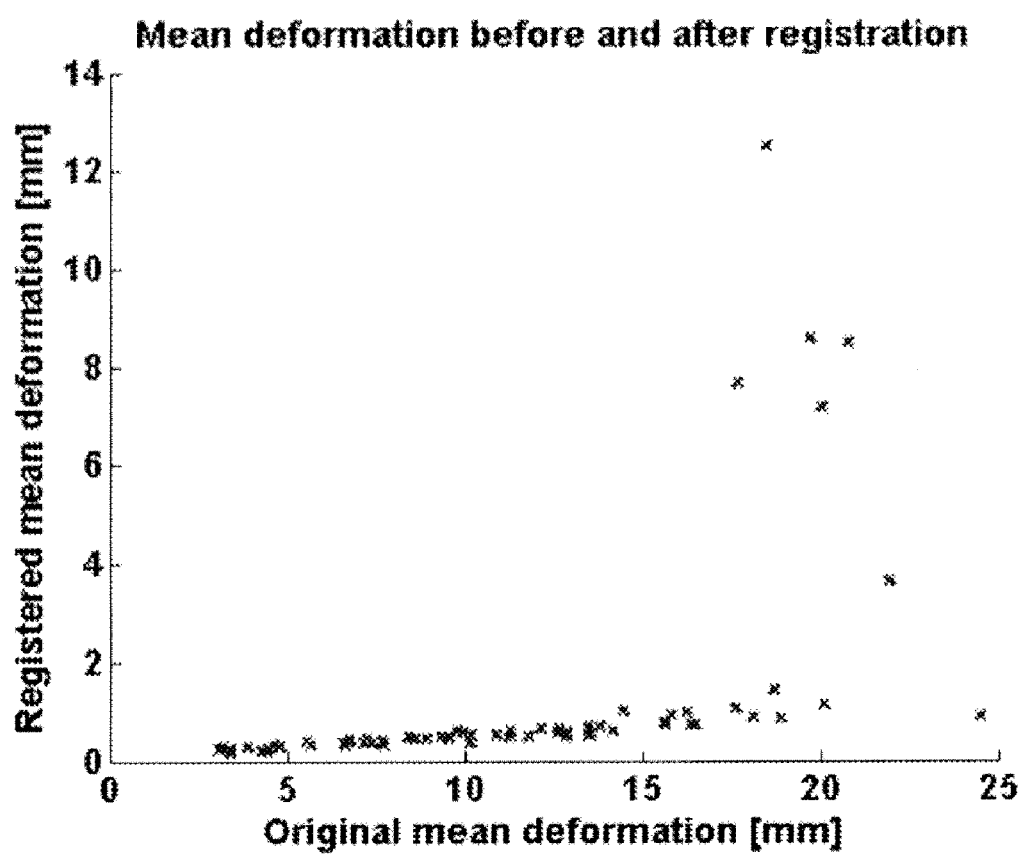
FIG. 15 shows resulting mean TPS registration error as a function of original image mean deformation.

The original MR was next registered with the homologous deformed MR using 4×4×2=32 control points using TPS for a total of 65 registrations. Note that a different configuration of control points was intentionally used for registration than for the original deformation. Even though TPS was used for the deformation, it was not possible to exactly recover the deformation using TPS with a different configuration of control points. TPS was used to perform the random deformations because of the availability of code readily available to compute the Jacobian of the deformation. Checking the resulting random deformations using the Jacobian indicated that the deformations were sometimes folding for mean error deformations of 10 mm or greater. As such, the negative Jacobian criteria was used to discard such deformations, and randomly regenerated others that satisfied the criteria of a non-negative Jacobian everywhere in the deformed dataset. The registration process was initialized using identically the same 5 control point loci for all homologous, deformed datasets. A multi-level registration approach was also used where the number of control points was systematically increased in stages such that the long range problem was solved first, and then iteratively worked at a smaller scale by using more points. Each new stage began with more control points placed in the homologous dataset based on the best optimization at the larger, previous scale. The displacement error was computed between the known deformation and the recovered deformation for 65 cases as shown in FIG. 15. FIG. 15 showed that up to original mean deformation approaching 18 mm, registration algorithm resulted in subvoxel displacement error (e.g., ~1 mm or less); above a 18 mm threshold the rate of capture became problematic.

Figures 16A, 16B, 16C:
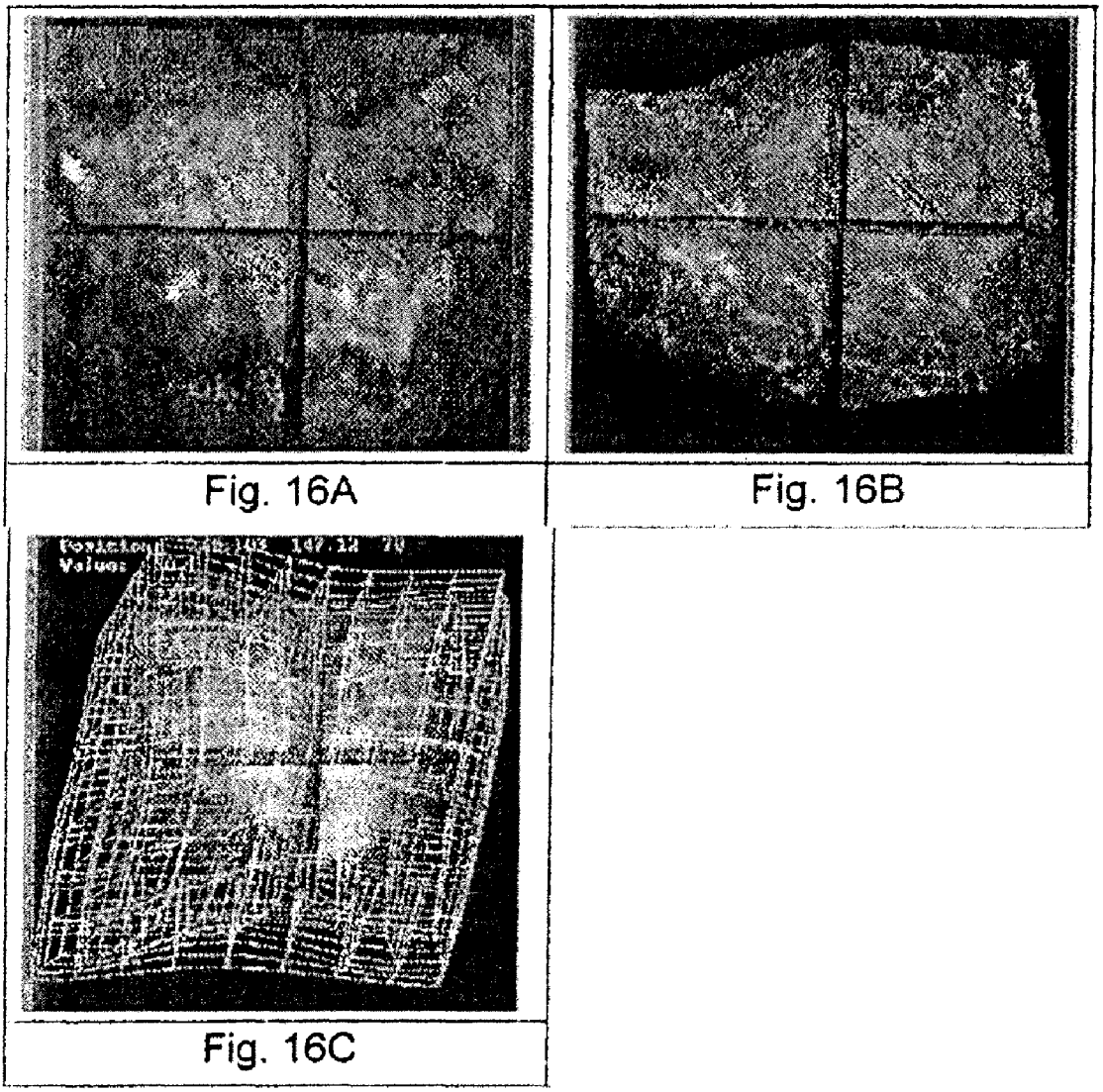
FIG. 16A shows a plane through original volume.
FIG. 16B shows a plane through deformed volume.
FIG. 16C shows deformation grid mapping volume A into B having a mean deformation of 17.6 mm.

FIGS. 16A, 16B, and 16C show examples where the deformed MR has a mean deformation of 17.62 mm but the maximum local deformation 46.51 mm. The non-zero slope of the recovered mean deformation was due to, for example, the smoothing artifact of trilinear interpolation in computing the resulting initially deformed dataset. The worse the deformation, the more distance between original pixels in the deformed dataset which increased the point spread function and increased the smoothing artifact.

Figure 17:
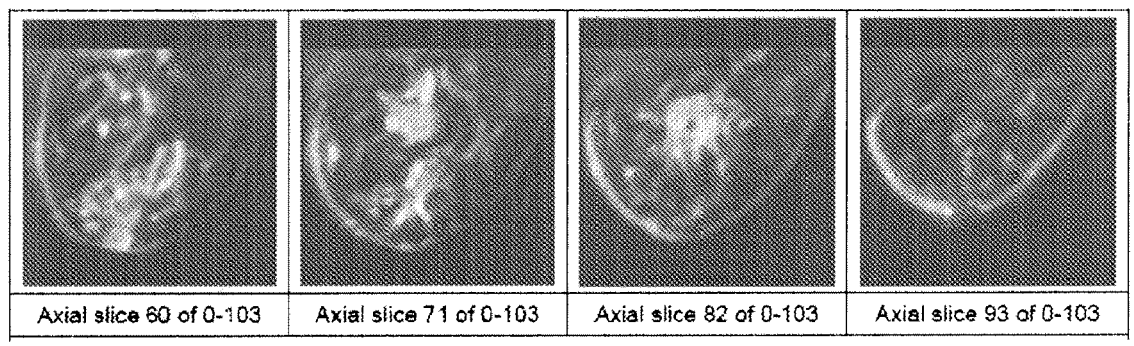
FIG. 17 shows four of 104 slices of a co-registered coronal DWI b0 baseline and repeat b0 baseline exams mapped onto T1_FatSat axial scan geometry.

FIG. 17 shows the automatic registration of a first breast diffusion image and a second breast diffusion image taken approximately an hour after the first breast diffusion image. The data was from a 1st patient volunteer using the 7-channel, sensecapable breast coil on the 3T Philips research magnet. These registered data sets came from two coronal b0-weighted DWI acquisitions separated by 15 minutes during which time the patient was removed from the magnet's table, and then returned to be repositioned and rescanned. The registration was demonstrated using alpha blending of the color combination of the two datasets by presenting the reference dataset in a bluegreen hue and the registered dataset in grayscale.

Figure 18:
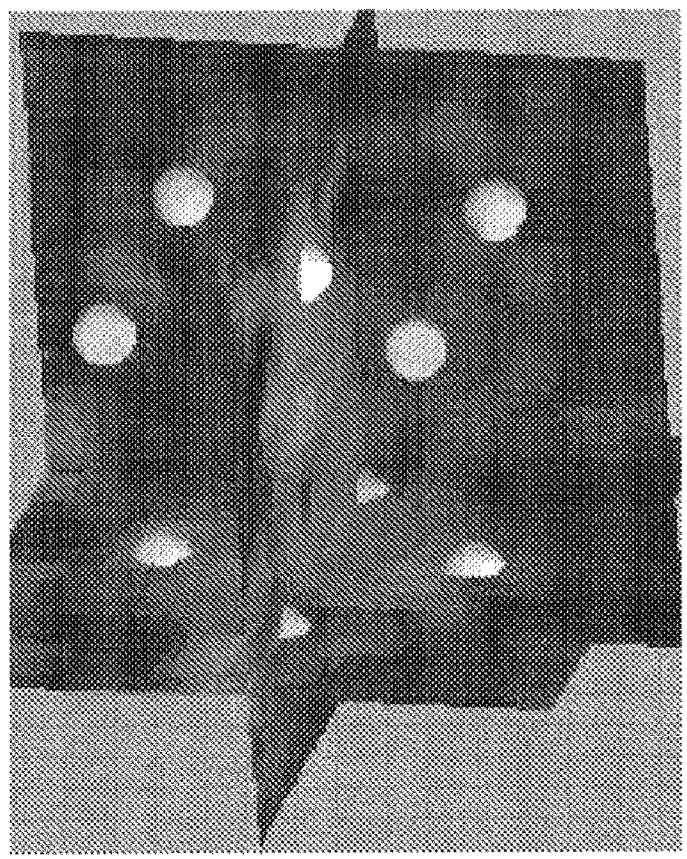
FIG. 18 shows three triads of control points in cropped volume of breast lesion displayed via 3 orthogonal cut planes.
Figure 19:
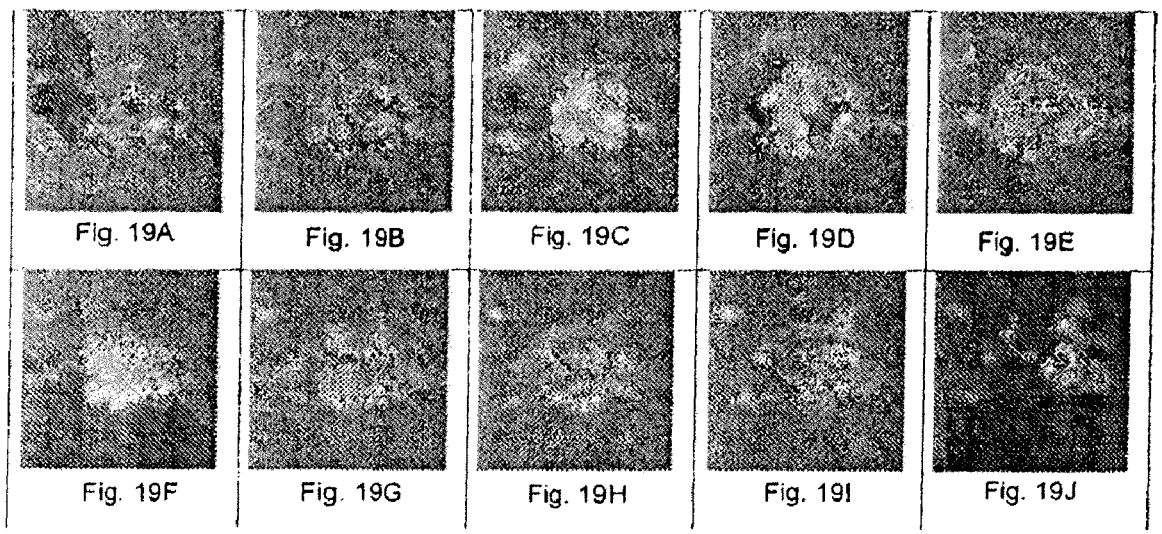
FIGS. 19A-19J show a series of coronal slices through the post-therapeutic primary breast lesion warped onto its pre-therapeutic scan ultimately using the 9 control points shown in FIG. 18.

While FIG. 17 was generated to show results typical of automatic registration of the whole breast, in the following section automatic registration was showed of just the lesion in the same patient for the pre- and post-chemotherapy exams. In FIG. 18, 3 triads of regularly spaced control points automatically generated based on the manually, tightly cropped volume bounds (35×35×18 voxels) containing principally just the primary breast lesion in the pre-therapeutic exam were shown. The warping results are shown in FIGS. 19A-19J where the coronal post-therapeutic b0 DWI lesion has been geometrically mapped (warped) onto the coronal pre-therapeutic b0 DWI reference lesion using just the 9 control points from the 3 triads. The two are shown using the alpha blended color combination of the two data sets where in this case the pre-therapeutic scan shown in the yellow hue was more visible for larger amplitudes. Misregistration was observed when the two "hues" (yellow in this case and grayscale) appeared separately with spatial offsets. Individual voxels are visible in this 35×35 coronal view.

Since the number of voxels that the algorithm must register is small, the warping registration computation times dropped proportionally anywhere from 1-2 hours to 1-2 minutes. Additionally the registration of the lesion was typically more accurate than that achieved by registration of the whole breast, which is needed since fDM is computed primarily for lesions. The schedule for this registration used the first 3 control points to rigidly align the two lesions, then with increased accuracy used 5 control points to grossly warp the two lesions, and finally used all 9 control points to refine the warping. The use of such schedules enables the algorithm to robustly and quickly capture the solution always working from larger to smaller scales. Such schedules are proforma for given control point configuration and density which in turn is driven by the information content of the image sets. Once a schedule is devised for the data from a particular scanner and sequence, it can be reused for other similar tasks with little, if any, revision. In some cases where the warping between the two data sets is excessive it may be necessary to start the schedule with a low degree of freedom warping solution (e.g., 5 control points in 3D) instead of initially using rotate/translate to support capture of the large scale warp as was done for the capture range experiment presented previously in FIG. 15. In some embodiments, as the mechanical elastic modulus of most tumors is typically orders of magnitude greater than the reminder of the breast, rigid registration for the first of the schedule's elements is all that is needed for registering a breast's primary lesion.

Example XII

Figure 20:
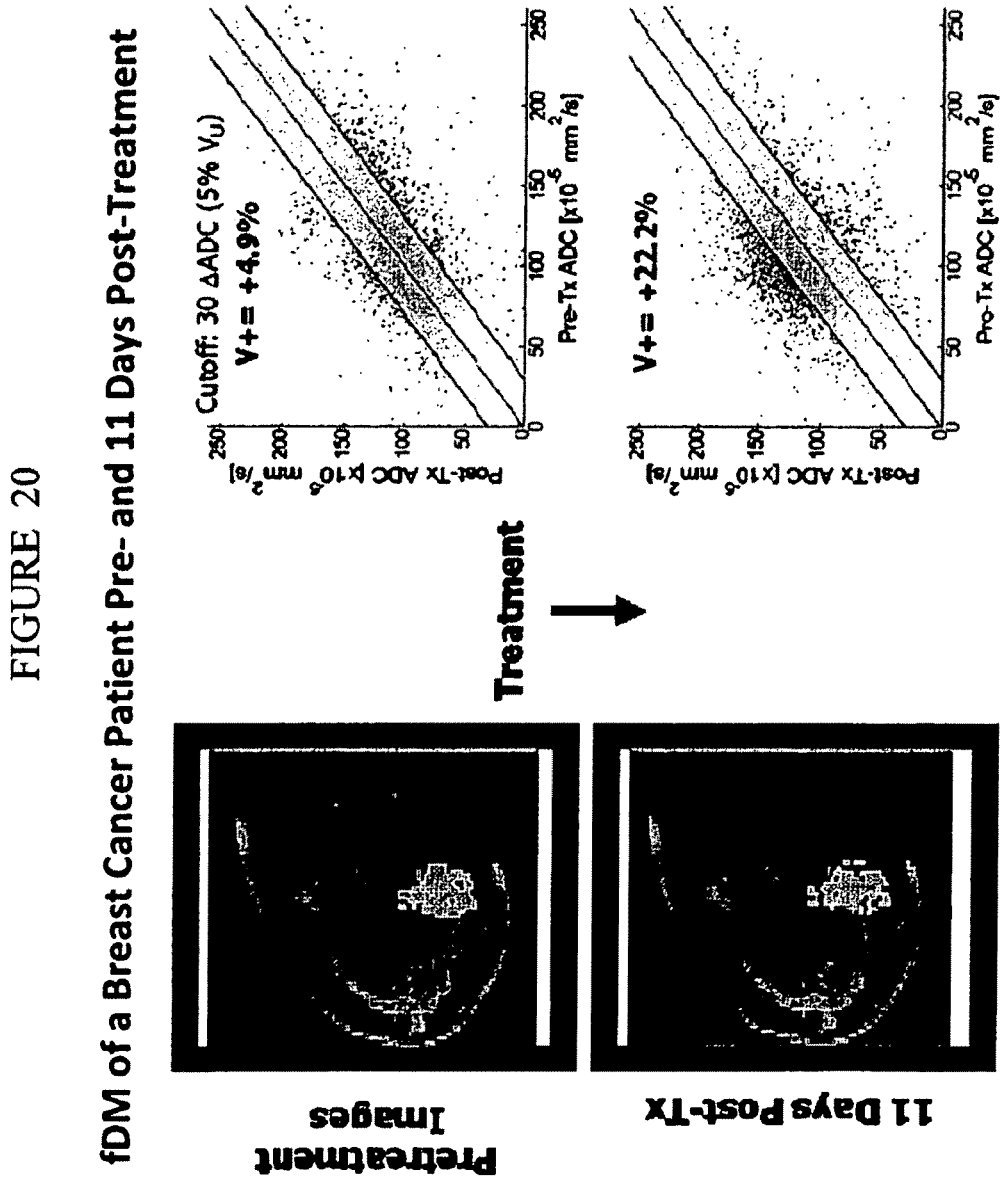
FIG. 20 shows fDM results of a breast cancer patient at baseline (Day 0; Top Left Panel) and at 11 days post-treatment initiation (Bottom Left Panel). Quantification of voxels which had increased diffusion can be accomplished using the associated scatter plots (Right Panels) wherein 22.2% of the tumor mass/volume had a significant increase in diffusion values at 11 days post-treatment induction. This figure reveals that fDM can detect early-on in treatment, response of a breast tumor.
Figure 21:
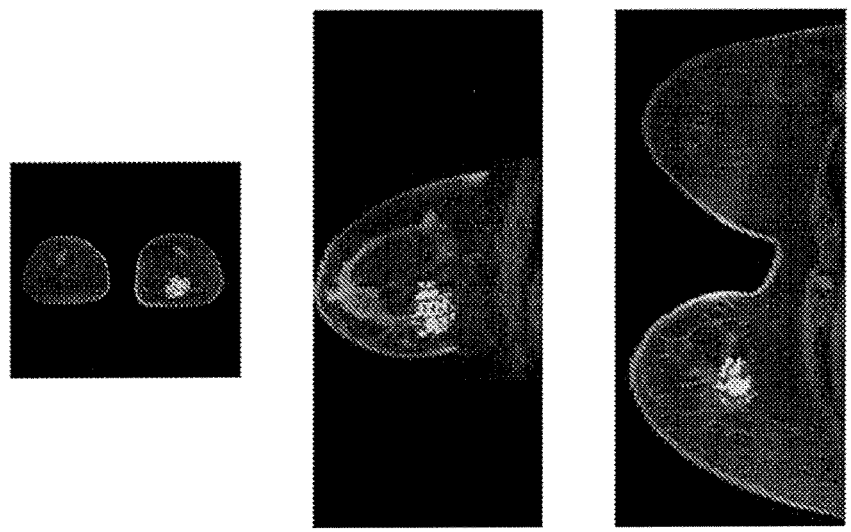
FIG. 21 shows fDM results in several different planes of view of a breast cancer patient at 11 days post treatment. The red regions reveal significant treatment effects upon the tumor mass as it indicates increased water diffusion had occurred due to killing of tumor cells in those regions.

This example shows fDM of a breast cancer patient before and after treatment initiation. Prior to receiving neoadjuvant chemotherapy, the breast cancer patient underwent 2 MRI to obtain data on variability of the fDM measurement. The first baseline MRI consisted of diffusion weighted imaging only. The second pre-treatment baseline MRI was performed in the same session as the first MRI. Following the first MRI, the breast cancer patient was taken off the MRI table for a short break and then repositioned onto the MRI table for the second baseline MRI. The entire session to obtain the two baseline MRIs took approximately 1.5 hours. The patient underwent an additional MRI scan 11 days after the first dose of neoadjuvant chemotherapy. FIG. 20 shows fDM of the breast cancer patient at Day 0 as a baseline fDM (Upper Left Panel) with the corresponding scatter plot (Upper Right Panel). Eleven days following treatment initiation an additional diffusion MRI scan was acquired and fDM data generated to assess treatment effects on tumor water diffusion values. Shown in FIG. 20 (Lower Left Panel) the fDM results for this tumor revealed significant increased diffusion values had occurred spatially which were encoded as red. The corresponding scatter plot (FIG. 20, Lower Right Panel) shows the data from the entire tumor volume. Each point represent a single voxel from the multi-slice tumor image data set. Increased tumor diffusion values are represented by the red points and analysis yielded a total of 22.2% of the entire tumor volume had a significant increase in diffusion at 11 days post-treatment initiation. This is very early into therapy and indicates that the image registration fDM algorithm was able to detect and quantify treatment response. FIG. 21 shows fDM data of a breast cancer patient at 11 days post treatment in several different orientations and planes through the tumor site.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for assessing an effectiveness of a treatment for a tissue region, the method comprising:
   obtaining a first set of water diffusion data for said tissue region with an MRI device configured to collect diffusion MRI data;
   obtaining, after administration of a treatment to said tissue region, a second set of water diffusion data for said tissue region with said MRI device;
   processing said first and second sets of water diffusion data with an algorithm to align said first and second sets of water diffusion data using at least a non-linear 3D warping deformation, wherein said algorithm comprises a plurality of schedule lines, each schedule line defining a set of parameters in its respective registration role, wherein each set of parameters includes an imposed image resolution, and wherein the image resolutions increase as a function of sequentially selected schedule lines;
   processing said first and second sets of water diffusion data with a functional diffusion map algorithm to generate a functional diffusion map for said tissue region, wherein said functional diffusion map characterizes spatially aligned tissue regions as having altered or unaltered water diffusion properties; and
   assessing the effectiveness of said administered treatment based on said functional diffusion map.

2. The method of claim 1, further comprising:
   assessing a temporal evolution of an untreated tissue region based on water diffusion properties.

3. The method of claim 1, wherein said tissue region is a whole body.

4. The method of claim 1, further comprising:
   assessing the effectiveness of said administered treatment based on water diffusion properties, wherein said assessing comprises indicating an effective treatment if said functional diffusion map characterizes said tissue region as having regions of changed water diffusion properties, and indicating an ineffective treatment if said functional diffusion map characterizes said tissue region as having regions of unchanged water diffusion properties.

5. The method of claim 1, wherein said tissue region comprises at least one of a brain, lung, prostate, breast, colon, rectum, bladder, ovaries, skin, liver, spine, bone, pancreas, cervix, lymph, thyroid, adrenal gland, salivary gland, sebaceous gland, testis, thymus gland, penis, uterus, trachea, heart, spleen, bladder wall, lymphatic node, and an entire living organism including a human body.

6. The method of claim 1, wherein said algorithm to align said first and second sets of water diffusion data comprises a warping algorithm.

7. The method of claim 1, wherein said treatment is a cancer treatment.

8. The method of claim 1, wherein said tissue region is not a brain tissue region.

9. The method of claim 1, wherein said processing said first and second sets of water diffusion data with said algorithm to align said first and second sets of water diffusion data comprises cropping an image of said tissue region to generate a cropped image and processing the first and second sets of water diffusion data associated with said cropped image using said algorithm.

10. The method of claim 1, wherein said first image resolution and second image resolution comprise a first decimated image and a second decimated image, respectively.

11. A method for analyzing treatment of a tissue region, the method comprising:
    obtaining a first set of water diffusion data for said tissue region with an MRI device configured to collect diffusion MRI data;
    obtaining a subsequent second set of water diffusion data for said tissue region with said MRI device;
    cropping a region of interest in an image of said tissue region;
    processing said first and second sets of water diffusion data associated with the region of interest with an algorithm to align said first and second sets of water diffusion data using at least a non-linear 3D warping deformation, wherein said algorithm comprises a plurality of schedule lines, each schedule line defining a set of parameters in its respective registration role, wherein each set of parameters includes an imposed image resolution, and wherein the image resolutions increase as a function of sequentially selected schedule lines;
    processing said first and subsequent second sets of water diffusion data with a functional diffusion map algorithm to generate a functional diffusion map for said whole tissue region, wherein said functional diffusion map characterizes said tissue region as having altered or unaltered water diffusion properties; and
    assessing an effectiveness of said treatment based on said functional diffusion map.

12. The method of claim 11, wherein said algorithm to align said first and second sets of water diffusion data comprises a warping algorithm.

13. A method for treating an individual diagnosed with cancer or assessing a therapy, the method comprising:
    identifying a treatment to target a tissue region within said individual, wherein said tissue region comprises a tumor;
    obtaining a first set of water diffusion data for said tissue region with an MRI device configured to collect diffusion MRI data;

obtaining, after administration of a treatment to said individual, a second set of water diffusion data for said tissue region with said MRI device;

processing said first and second sets of water diffusion data with an algorithm to align said first and second sets of water diffusion data using at least a non-linear 3D warping deformation, wherein said algorithm comprises a plurality of schedule lines, each schedule line defining a set of parameters in its respective registration role, wherein each set of parameters includes an imposed image resolution, and wherein the image resolutions increase as a function of sequentially selected schedule lines;

processing said first and second sets of water diffusion data with a functional diffusion map algorithm to generate a functional diffusion map for said tissue region, wherein said functional diffusion map characterizes said tissue region as having altered or unaltered water diffusion properties; and assessing an effectiveness of said administered treatment based on said functional diffusion map.

14. The method of claim 13, further comprising:

assessing the effectiveness of said administered treatment, wherein said assessing comprises indicating an effective treatment if said functional diffusion map characterizes said tissue region as having regions of altered water diffusion properties.

15. The method of claim 13, further comprising:

adapting said treatment, wherein said adapting comprises modifying said treatment based on one or more results from said functional diffusion map.

16. The method of claim 13, wherein said tissue region comprises at least one of a bone, lung, prostate, breast, colon, rectum, bladder, ovaries, skin, liver, spine, bone, pancreas, cervix, lymph, thyroid, adrenal gland, salivary gland, sebaceous gland, testis, thymus gland, penis, uterus, trachea, heart, spleen, bladder wall, lymphatic node, and an entire living organism including a human body.

17. The method of claim 13, wherein said algorithm to align said first and second sets of water diffusion data comprises a warping algorithm.

18. The method of claim 13, further comprising:

obtaining, after said second set of water diffusion data, one or more additional sets of water diffusion data for said tissue region.

19. The method of claim 13, wherein said processing the first and second sets of water diffusion data with said functional diffusion map algorithm comprises automatically processing the first and second sets of water diffusion data with said functional diffusion map algorithm after said obtaining said second set of water diffusion data.

20. A system for assessing an effectiveness of a treatment for a tissue region, the system comprising:

a first processing device configured to:
receive a first set of water diffusion data for said tissue region from an MRI device; and
receive, after administration of a treatment to said tissue region, a second set of water diffusion data for said tissue region from said MRI device;

a second processing device configured to process said first and second sets of water diffusion data with an algorithm to align said first and second sets of water diffusion data using at least a non-linear 3D warping deformation, wherein said algorithm comprises plurality of schedule lines, each schedule line defining a set of parameters in its respective registration role, wherein each set of parameters includes an imposed image resolution, and wherein the image resolutions increase as a function of sequentially selected schedule lines; and a third processing device configured to process said first and second sets of water diffusion data with a functional diffusion map algorithm to generate a functional diffusion map for said tissue region, wherein said functional diffusion map characterizes spatially aligned tissue regions as having altered or unaltered water diffusion properties.

* * * * *

UNITED STATES PATENT AND TRADEMARK OFFICE
CERTIFICATE OF CORRECTION

PATENT NO. : 8,185,186 B2
APPLICATION NO. : 12/101753
DATED : May 22, 2012
INVENTOR(S) : Brian D. Ross et al.

Page 1 of 1

It is certified that error appears in the above-identified patent and that said Letters Patent is hereby corrected as shown below:

On the Title page, the Inventors item (75) reads:

Brian D. Ross, Ann Arbor, MI (US); Alnawaz Rehemtulla, Plymouth, MI (US); Thomas L. Chenevert, Ann Arbor, MI (US); Charles R. Meyer, Ann Arbor, MI (US); Kuei C. Lee, San Antonio, TX (US); Kenneth Pienta, Ann Arbor, MI (US); Maha Hussein, Ann Arbor, MI (US), Anne Schott, Ann Arbor, MI (US).

On the Title page, the Inventors item (75) should read:

Brian D. Ross, Ann Arbor, MI (US); Alnawaz Rehemtulla, Plymouth, MI (US); Thomas L. Chenevert, Ann Arbor, MI (US); Charles R. Meyer, Ann Arbor, MI (US); Kuei C. Lee, San Antonio, TX (US); Kenneth Pienta, Ann Arbor, MI (US); Maha Huss<u>a</u>in, Ann Arbor, MI (US), Anne Schott, Ann Arbor, MI (US).

Signed and Sealed this
Second Day of June, 2015

Michelle K. Lee
*Director of the United States Patent and Trademark Office*